United States Patent
Dubnau et al.

(10) Patent No.: US 9,422,605 B2
(45) Date of Patent: Aug. 23, 2016

(54) TRANSPOSON ACTIVATION DURING AGING AND NEURONAL DECLINE

(71) Applicant: Cold Spring Harbor Laboratory, Cold Spring Harbor, NY (US)

(72) Inventors: Joshua Dubnau, Huntington, NY (US); Wanhe Li, New York, NY (US); Lisa Prazak, Massapequa Park, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 0 days.

(21) Appl. No.: 14/216,491

(22) Filed: Mar. 17, 2014

(65) Prior Publication Data

US 2014/0377758 A1 Dec. 25, 2014

Related U.S. Application Data

(60) Provisional application No. 61/798,994, filed on Mar. 15, 2013.

(51) Int. Cl.
*C07H 21/02* (2006.01)
*C07H 21/04* (2006.01)
*C12Q 1/68* (2006.01)

(52) U.S. Cl.
CPC ............ *C12Q 1/6881* (2013.01); *C12Q 1/6883* (2013.01); *C12Q 2600/118* (2013.01); *C12Q 2600/158* (2013.01)

(58) Field of Classification Search
CPC . C12N 15/113; C12N 15/111; C12N 2310/11
See application file for complete search history.

(56) References Cited

FOREIGN PATENT DOCUMENTS

WO WO-2011/017404 A2 2/2011

OTHER PUBLICATIONS

Johnson et al., "The Role of DNA Methylation in Aging, Rejuvenation and Age-Related Disease", Rejuvenation Research, 2012, vol. 15, No. 5, pp. 483-494.
Li et al., "Transposable Elements in TDP-43-Mediated Neurodegenerative Disorders", PLoS One, 2012, vol. 7, No. 9, e44099, pp. 1-10.
Perrat, "Transposition Driven Genomic Heterogeneity in the *Drosophila* Brain: A Dissertation", University of Massachusetts Medical School, GSBS Dissertations and Thesis, 2012, Paper 622, pp. 1-121.
St Laurent et al., "A LINE-1 Component to Human Aging: Do LINE Elements Exact a Longevity Cost for Evolutionary Advantage?", Mechanisms of Ageing and Development, 2010, vol. 131, pp. 299-305.
Woodruff et al., "P DNA Element Movement in Somatic Cells Reduces Lifespan in *Drosophila melanogaster*: Evidence in Support of the Somatic Mutation Theory of Aging", Mutation Research, 1995, vol. 338, pp. 35-42.
International Search Report for Application No. PCT/US14/30408, mailed Nov. 13, 2014.
Chung et al., "Endogenous RNA Interference Provides a Somatic Defense Against *Drosophila* Transposons", Curr Biol., 2008, vol. 18, No. 11, pp. 795-802.

*Primary Examiner* — Amy Bowman
(74) *Attorney, Agent, or Firm* — McCarter & English, LLP

(57) ABSTRACT

The present invention relates to transposon activation and mobilization, particularly in the brain, during normal aging; reporter systems to detect such mobilization, along with cells and transgenic animals containing such systems; methods of monitoring neuronal function during normal aging; methods of determining the risk of age-related neuronal decline and age-related mortality; and the use of transposon inhibitors and apoptosis inhibitors to delay age-related neuronal decline and age-related mortality.

20 Claims, 21 Drawing Sheets

SEQUENCE LISTING

```
<160> NUMBER OF SEQ ID NOS: 21

<210> SEQ ID NO 1
<211> LENGTH: 17
<212> TYPE: DNA
<213> ORGANISM: Artificial Sequence
<220> FEATURE:
<223> OTHER INFORMATION: Probe

<400> SEQUENCE: 1
acatacgcca taatctg                                                    17

<210> SEQ ID NO 2
<211> LENGTH: 24
<212> TYPE: DNA
<213> ORGANISM: Artificial Sequence
<220> FEATURE:
<223> OTHER INFORMATION: PROBE

<400> SEQUENCE: 2
tcggtgcata acttagttag ttca                                            24

<210> SEQ ID NO 3
<211> LENGTH: 20
<212> TYPE: DNA
<213> ORGANISM: Artificial Sequence
<220> FEATURE:
<223> OTHER INFORMATION: PROBE

<400> SEQUENCE: 3
aagcatttgt gtttgatttc                                                 20

<210> SEQ ID NO 4
<211> LENGTH: 16
<212> TYPE: DNA
<213> ORGANISM: Artificial Sequence
<220> FEATURE:
<223> OTHER INFORMATION: PROBE

<400> SEQUENCE: 4
cccgatctgg gttgtc                                                     16

<210> SEQ ID NO 5
```

```
<211> LENGTH: 21
<212> TYPE: DNA
<213> ORGANISM: Artificial Sequence
<220> FEATURE:
<223> OTHER INFORMATION: probe

<400> SEQUENCE: 5
ccccatgatt agtctttact g                                              21

<210> SEQ ID NO 6
<211> LENGTH: 20
<212> TYPE: DNA
<213> ORGANISM: Artificial Sequence
<220> FEATURE:
<223> OTHER INFORMATION: probe

<400> SEQUENCE: 6
aagctgaaga ctgatttatg                                                20

<210> SEQ ID NO 7
<211> LENGTH: 25
<212> TYPE: DNA
<213> ORGANISM: Artificial Sequence
<220> FEATURE:
<223> OTHER INFORMATION: PROBE

<400> SEQUENCE: 7
ttgatcaaac atacaaatta attac                                          25

<210> SEQ ID NO 8
<211> LENGTH: 25
<212> TYPE: DNA
<213> ORGANISM: Artificial Sequence
<220> FEATURE:
<223> OTHER INFORMATION: PROBE

<400> SEQUENCE: 8
gaatgccatt ccaaatggag agccc                                          25

<210> SEQ ID NO 9
<211> LENGTH: 25
<212> TYPE: DNA
<213> ORGANISM: Artificial Sequence
<220> FEATURE:
<223> OTHER INFORMATION: PROBE

<400> SEQUENCE: 9
tagaaaaata ttgggcgaac aagtt                                          25

<210> SEQ ID NO 10
<211> LENGTH: 21
<212> TYPE: DNA
<213> ORGANISM: Artificial Sequence
<220> FEATURE:
<223> OTHER INFORMATION: PROBE

<400> SEQUENCE: 10
cctattagtg atccgctcgc g                                              21

<210> SEQ ID NO 11
<211> LENGTH: 18
<212> TYPE: DNA
<213> ORGANISM: Artificial Sequence
<220> FEATURE:
<223> OTHER INFORMATION: PROBE
```

<400> SEQUENCE: 11
cttcgatccg aggtatgc                                                    18

<210> SEQ ID NO 12
<211> LENGTH: 22
<212> TYPE: DNA
<213> ORGANISM: Artificial Sequence
<220> FEATURE:
<223> OTHER INFORMATION: PROBE

<400> SEQUENCE: 12
aaggtagtag gttacatttg tc                                               22

<210> SEQ ID NO 13
<211> LENGTH: 18
<212> TYPE: DNA
<213> ORGANISM: Artificial Sequence
<220> FEATURE:
<223> OTHER INFORMATION: PROBE

<400> SEQUENCE: 13
ccgtagtccg atggttcc                                                    18

<210> SEQ ID NO 14
<211> LENGTH: 21
<212> TYPE: DNA
<213> ORGANISM: Artificial Sequence
<220> FEATURE:
<223> OTHER INFORMATION: PROBE

<400> SEQUENCE: 14
ctgaggcttc tcttgtttaa t                                                21

<210> SEQ ID NO 15
<211> LENGTH: 17
<212> TYPE: DNA
<213> ORGANISM: Artificial Sequence
<220> FEATURE:
<223> OTHER INFORMATION: PROBE

<400> SEQUENCE: 15
ttgtcgacgc aattctt                                                     17

<210> SEQ ID NO 16
<211> LENGTH: 20
<212> TYPE: DNA
<213> ORGANISM: Artificial Sequence
<220> FEATURE:
<223> OTHER INFORMATION: PROBE

<400> SEQUENCE: 16
tcatagatga tgtcaaattt                                                  20

<210> SEQ ID NO 17
<211> LENGTH: 21
<212> TYPE: DNA
<213> ORGANISM: Artificial Sequence
<220> FEATURE:
<223> OTHER INFORMATION: PROBE

<400> SEQUENCE: 17
cagacaattt ctcagaatca t                                                21

```
<210> SEQ ID NO 18
<211> LENGTH: 20
<212> TYPE: DNA
<213> ORGANISM: Artificial Sequence
<220> FEATURE:
<223> OTHER INFORMATION: PRIMER

<400> SEQUENCE: 18
caactctgca cccacgacta                                                20

<210> SEQ ID NO 19
<211> LENGTH: 20
<212> TYPE: DNA
<213> ORGANISM: Artificial Sequence
<220> FEATURE:
<223> OTHER INFORMATION: PRIMER

<400> SEQUENCE: 19
cagcggaaag ctgacacttc                                                20

<210> SEQ ID NO 20
<211> LENGTH: 20
<212> TYPE: DNA
<213> ORGANISM: Artificial Sequence
<220> FEATURE:
<223> OTHER INFORMATION: PRIMER

<400> SEQUENCE: 20
cacacaccca tggaattgaa                                                20

<210> SEQ ID NO 21
<211> LENGTH: 20
<212> TYPE: DNA
<213> ORGANISM: Artificial Sequence
<220> FEATURE:
<223> OTHER INFORMATION: PRIMER

<400> SEQUENCE: 21
ggctcattgc cgttaaacat                                                20
```

TRANSPOSON ACTIVATION DURING AGING AND NEURONAL DECLINE

CROSS-REFERENCE TO RELATED APPLICATIONS

This application claims the benefit under 35 U.S.C. §119(e) to U.S. Provisional Application No. 61/798,994, filed Mar. 15, 2013, which is incorporated herein by reference in its entirety.

STATEMENT OF GOVERNMENT INTEREST

This invention was made with government support under Grant Number 5R01 NS067690-05 awarded by the National Institutes of Health (NIH). The government has certain rights in the invention.

FIELD OF THE INVENTION

The present invention relates to transposon activation and mobilization, particularly in the brain during normal aging; reporter systems to detect such mobilization; methods of monitoring neuronal function during normal aging; methods of determining the risk of age-related neuronal decline and age-related mortality; and the use of transposon inhibitors and apoptosis inhibitors to delay age-related neuronal decline and age-related mortality.

BACKGROUND OF THE INVENTION

Transposable elements (TEs; or transposons) are highly abundant mobile genetic elements that comprise multiple classes and constitute a large fraction of most eukaryotic genomes. The class known as retrotransposons, for example, comprises about 40 and 30 percent of the human and *Drosophila* genomes, respectively. (Belancio et al., *Genome Res.* 2008, 18, 343-358; Goodier and Kazazian, *Cell* 2008, 135, 23-35; 2-5).

The movement and accumulation of TEs has been a major force in shaping the genes and genomes of almost all organisms. (Feschotte and Pritham, *Annu. Rev. Genet.* 2007, 41, 331-368; Hancks and Kazazian, *Curr. Opin. Gen. Dev.* 2012, 22, 191-202; Burns and Boeke, *Cell* 2012, 149, 740-752). This force is not without potential adverse consequences, however: TEs represent a massive reservoir of potential genomic stability and RNA-level toxicity that must also be kept in check. Indeed, many TE appear static and non-functional.

However, at least some TEs are capable of replicating and mobilizing to new positions in the genome—and even immobile TE copies can be expressed. And endogenous transposition itself has been detected in the germline—where TEs have been most extensively investigated (Belancio et al., *Genome Res.* 2008, 18, 343-358). In addition, somatic transposition events have observed in early embryonic development and during neurogenesis. (Goodier and Kazazian, *Cell* 2008, 135, 23-35; 2-5; Muotri et al., *Nature* 2010, 468, 443-446; Baillie et al., *Nature* 2011, 479, 534-537; Coufal et al., *Proc. Natl. Acad. Sci. USA* 2011, 108, 20382-20387).

These observations do not, however, address the extent to which TEs are expressed or mobilized in the brain during normal aging—much less the possible functional consequences of such activation. Clarifying these issues may afford new mechanistic insights into aging and related physiological processes. The present invention meets these and other needs in art, providing new tools, along with new diagnostic and therapeutic methods, as disclosed herein.

SUMMARY OF THE INVENTION

In a first set of embodiments, the invention provides methods of monitoring neuronal function during normal aging, comprising measuring expression of at least one transposon in a biological sample from a subject and determining whether the measured transposon expression exceeds a predetermined level.

In a second set of embodiments, the invention provides methods of determining the risk of age-related neuronal decline (or age-related mortality). These methods comprise measuring expression of at least transposon in a biological sample from a subject, and determining whether the measured transposon expression exceeds a predetermined level, wherein measured transposon expression that exceeds the predetermined level indicates that the subject is at risk of accelerated age-related neuronal decline (or accelerated age-related mortality). In a specific aspect, the age-related neuronal decline is a cognitive decline, in particular an impairment in memory, and more particularly, an impairment in long-term memory.

In the first and second set of embodiments, the transposon can be a DNA transposon, and more particularly, an autonomous element or a nonautonomous element. The transposon can also be a retrotransposon, including an LTR retrotransposon and a non-LTR retrotransposon. More specifically, an LTR retrotransposon can include a gypsy element or an endogengous retrovirus (ERV); and a non-LTR retrotransposon can include a SINE retrotransposon, such as an Alu sequence; a LINE element, such as L1, or a LINE-like element, such as R1 or R2.

In a more specific aspect, the first and second embodiments can also include administering to the subject an effective amount of a transposon inhibitor or an apoptosis inhibitor.

In a third set of embodiments, the invention provides methods of delaying age-related neuronal decline or age-related mortality, comprising administering to a subject in need of such treatment an effective amount of a transposon inhibitor or apoptosis inhibitor. In a specific aspect, the age-related neuronal decline is a cognitive decline, in particular an impairment in memory, and more particularly, an impairment in long-term memory.

As used in the first, second, and third embodiments, the transposon inhibitor may be an inhibitor of a protein encoded by a transposon, such as an inhibitor of a transposase, an integrase, a reverse transcriptase, an endonuclease; a protein encoded by gag, pol, or env; an enzyme encoded by ORF1 of a non-LTR transposon; or an enzyme encoded by ORF2 of a non-LTR transposon. The transposon inhibitor can also be an anti-retroviral drug; an inhibitor of reverse transcription; an inhibitor of transposase or integrase activity; an inhibitor of endonuclease activity; a stimulator of DNA repair machinery; a zinc-finger that targets a transposon promoter region; a repressor that inhibits a transposon; an innate antiretroviral resistance factor; a small interfering RNAs (siRNA), short hairpin RNA (shRNA), morpholino, or antisense oligonucleotide directed to a TE transcript; or an inhibitor of post-translational processing or proteolysis of a transposon-encoded proteins. The transposon inhibitor may also be an agent that blocks intercellular transmission of transposon genetic material or protein, such as an agent that prevents binding of a viral particle to a cell surface receptor.

As used in the first, second, and third embodiments, the apoptosis inhibitor includes an inhibitor of a checkpoint kinase, and Checkpoint kinase 2, in particular. Apoptosis inhibitors also include stimulators of the DNA repair machinery, as well as endogenous inhibitors of apoptosis, such as those in human Inhibitor of Apoptosis (IAP) family, whose members include Cp-IAP, Op-IAP, XIAP, c-IAP1, c-IAP2, NAIP, and surviving. An apoptosis inhibitor can also include antagonists directed to pro-apoptotic proteins such as a caspase, Bak, and Bax, and agonists directed to anti-apoptotic proteins such as Bcl-1.

In one aspect of the methods, the subject is an invertebrate, more particularly, *Drosophila*. In another aspect, the subject is a vertebrate, particularly a mammal, more particularly, a human, and even more particularly, a healthy human.

In another aspect of the methods, the transposon inhibitor or apoptosis inhibitor is formulated as a pharmaceutical composition and is administered to the subject in a therapeutically effective amount. The inhibitor may also be administered together or in conjunction with other agents.

In other embodiments, the invention provides a recombinant nucleic acid sequence for detecting de novo TE integration events, comprising a promoter region; a reporter gene operably linked to the promoter; and a fragment inserted between the promoter and reporter gene, wherein the fragment comprises binding sites that are necessary and sufficient to attract de novo TE insertions, and does not itself does not disrupt expression of the reporter gene. In a specific aspect, the reporter gene encodes an expression disrupter, which can include GAL80. In another aspect, the fragment is an ovo regulatory region containing multiple Ovo binding sites.

The present invention also include a cell comprising any of the disclosed recombinant nucleic acid sequences. Such a cell may also include a second recombinant nucleic acid sequence, comprising a second promoter region operably linked to a second reporter gene, wherein expression of the second reporter gene is blocked by the expression disrupter. In a particular aspect, expression of the second reporter gene is mediated by GAL4. The invention also includes a transgenic animal, including a transgenic vertebrate or transgenic *Drosophila*, comprising any of the recombinant nucleic sequences herein (or cell that contains any of them).

More generally, the invention is further directed to the general and specific embodiments defined, respectively, by the independent and dependent claims appended hereto, which are incorporated by reference herein.

BRIEF DESCRIPTION OF FIGURES

For a more complete understanding of the invention, reference is now made to the Detailed Description and Examples in conjunction with the accompanying figures.

FIG. 5A is an illustration of the design and operation of the "gypsy-TRAP." A ~500 bp fragment from the ovo regulatory region containing 5 Ovo binding sites is inserted between Tub promoter and GAL80 gene. A mutated "gypsy-TRAP" construct contains mutations that disrupt each of the 5 Ovo binding sites. In the absence of gypsy insertions, GAL80 expression suppresses GAL4, and UAS::mCD8::GFP is not expressed. In the presence of gypsy integration into the "gypsy-TRAP", GAL80 expression is blocked, and UAS::mCD8::GFP is turned on.

DETAILED DESCRIPTION OF THE INVENTION

Figure 1A:
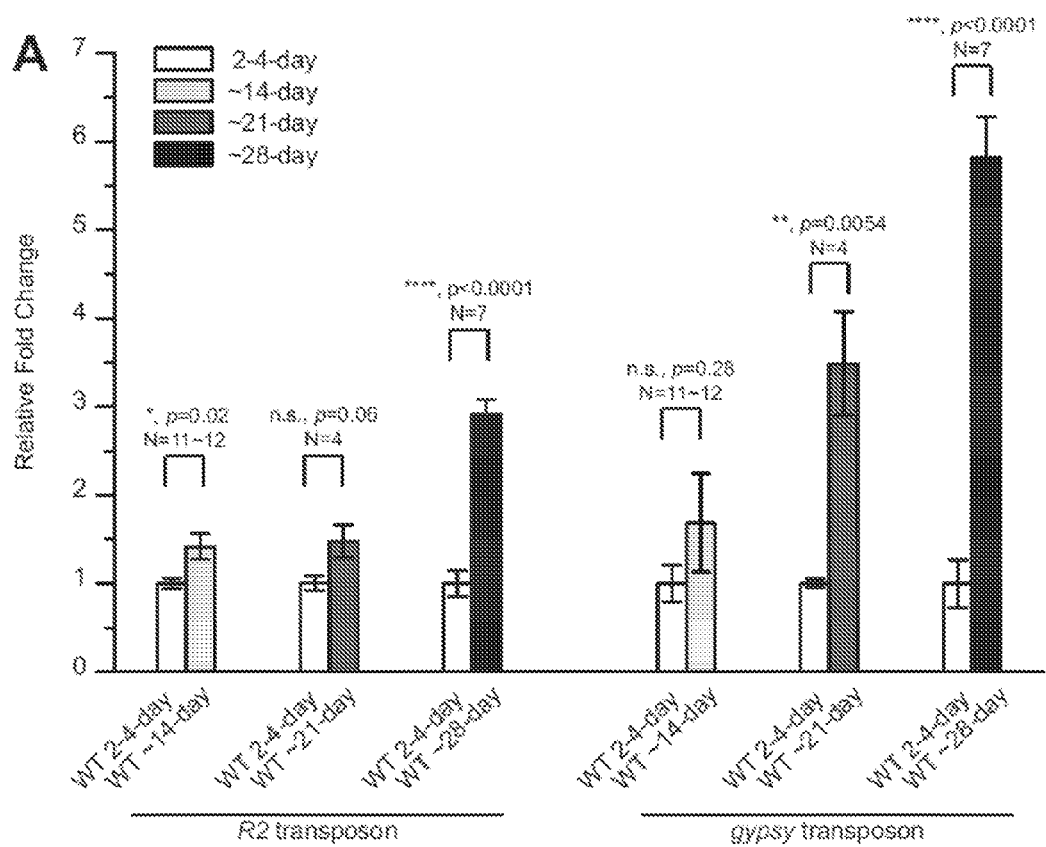
FIG. 1A is a histogram showing age-dependent expression of transposable elements in normal *Drosophila* brain. Levels of transcripts of R2, a LINE-like element and gypsy, an LTR element were quantified by QPCR with RNA preparations from young (2-4-day) and aged (~14-day, ~21-day and ~28-day) wild type (WT) fly heads. Levels of TE transcripts are normalized to Actin. Expression shown as fold changes relative to WT (means±SEM).

The invention may be more fully appreciated by reference to the following description, including the Examples. Unless otherwise defined, all technical and scientific terms used herein have the same meaning as commonly understood by one of ordinary skill in the pharmaceutical arts. Although methods and materials similar or equivalent to those described herein can be used in the practice or testing of the present invention, suitable methods and materials are described herein. In addition, the materials, methods, and examples are illustrative only and are not intended to be limiting.

General reference is made to standard textbooks of molecular biology and pharmaceutics that contain definitions and methods and means for carrying out basic techniques, which may be encompassed by the present invention. See, e.g., Current Protocols in Pharmacology, Enna et al. (eds.), John Wiley and Sons, Inc., Hoboken, N.J. (2011), Current Protocols in Molecular Biology, Ausubel et al. (eds.), John Wiley & Sons, Inc., Hoboken, N.J. (2011), Current Protocols in Cell Biology, Bonifacino et al. (eds.), John Wiley & Sons, Inc.: Hoboken, N.J. (2011); Current Protocols in Neuroscience, Gerfen et al. (eds.), John Wiley & Sons, Inc., Hoboken, N.J. (2011); and the various references cited therein.

All publications, including patent applications, patents, and other citations mentioned herein, are incorporated by reference in their entirety. Citation of any such publication, however, shall not be construed as an admission that it is prior art to the present invention.

Terms and Definitions

The use of subheadings such as "General," "Compositions," Formulations," etc., in this section, as well as in other sections of this application, are solely for convenience of reference and not intended to be limiting.

General

As used herein, the term "about" or "approximately" means within an acceptable range for a particular value as determined by one skilled in the art, and may depend in part on how the value is measured or determined, e.g., the limitations of the measurement system or technique. For example, "about" can mean a range of up to 20%, up to 10%, up to 5%, or up to 1% or less on either side of a given value. Alternatively, with respect to biological systems or processes, the term "about" can mean within an order of magnitude, within 5-fold, or within 2-fold on either side of a value. Numerical quantities given herein are approximate unless stated otherwise, meaning that the term "about" or "approximately" can be inferred when not expressly stated To provide a more concise description, some of the quantitative expressions given herein are not qualified with the term "about". It is understood that, whether the term "about" is used explicitly or not, every quantity given herein is meant to refer to the actual given value, and it is also meant to refer to the approximation of such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity for which that could be obtained under the particular stoichiometric conditions. Concentrations that are given as percentages refer to mass ratios, unless indicated differently.

As used herein, the terms "a," "an," and "the" are to be understood as meaning both singular and plural, unless explicitly stated otherwise. Thus, "a," "an," and "the" (and grammatical variations thereof where appropriate) refer to one or more.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof, unless limitation to the singular is explicitly stated.

The terms "comprising" and "including" are used herein in their open, non-limiting sense. Other terms and phrases used in this document, and variations thereof, unless otherwise expressly stated, should be construed as open ended, as opposed to limiting. As examples of the foregoing: the term "example" is used to provide exemplary instances of the item in discussion, not an exhaustive or limiting list thereof; adjectives such as "conventional," "traditional," "normal," "criterion," "known" and terms of similar meaning should not be construed as limiting the item described to a given time period or to an item available as of a given time, but instead should be read to encompass conventional, traditional, normal, or criterion technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. As will become apparent to one of ordinary skill in the art after reading this document, the illustrated embodiments and their various alternatives may be implemented without confinement to the illustrated examples.

Agents and Compositions

The terms "pharmaceutical agent," "agent," "compound," or "drug" may be used interchangeably herein, and include pharmacologically active substances in isolated form, or mixtures thereof. For example, a pharmaceutical agent, compound or drug may be an isolated and structurally-defined product, an isolated product of unknown structure, a mixture of several known and characterized products, or an undefined composition comprising one or more products. Examples of such undefined compositions include for instance tissue samples, biological fluids, cell supernatants, vegetal preparations, etc. The pharmaceutical agent, compound or drug may be any organic or inorganic product, including a polypeptide (or a protein or peptide), a nucleic acid, a lipid, a polysaccharide, a chemical entity, or mixture or derivatives thereof. The pharmaceutical agent, compound or drug may be of natural or synthetic origin, and the compound(s) or modulators may include libraries of compounds. In particular embodiments, the nucleic acid may comprise an inhibitory RNA molecule such as an siRNA, shRNA, or mico-RNA.

A pharmaceutical agent can decrease the amount, degree, or nature of transposon expression in vivo, in vitro, or ex vivo, relative to the amount, degree, or nature of transposon expression in the absence of the agent or reagent. In certain embodiments, treatment with such a pharmaceutical agent, such as a transposon inhibitor, may decrease the amount, degree, or nature of transposon expression by at least about 1%, 2%, 3%, 4%, 5%, 10%, 20%, 40%, 50%, 60%, 70%, 80%, 90%, or 100%, compared to the amount, degree, or nature of transposon expression in the absence of the agent, under the conditions of the method used to detect or determine transposon expression.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation, or aggregation of any two or more of the ingredients, or from dissociation of one or more of the ingredients, or from other types of reactions or interactions of one or more of the ingredients.

As used herein, the phrase "pharmaceutically acceptable" refers to molecular entities and compositions that are generally regarded as "safe," e.g., that are physiologically tolerable and do not typically produce an allergic or similar untoward reaction, such as gastric upset, dizziness and the like, or other significant adverse events, when administered to a human. Preferably, as used herein, the term "pharmaceutically acceptable" means approved by a regulatory agency of the Federal or a state government of listed in the U.S. Pharmacopeia or other generally recognized pharmacopeia for use in animals, and more particularly in humans.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluents to facilitate administration of an agent and that is compatible therewith. Examples of excipients include calcium carbonate, calcium phosphate, various sugars and types of starch, cellulose derivatives, gelatin, vegetable oils, and polyethylene glycols. Suitable pharmaceutical carriers include those described in Remington: The Science and Practice of Pharmacy, $21^{st}$ Ed., Lippincott Williams & Wilkins (2005).

The term "carrier" refers to an adjuvant, vehicle, or excipient, with which the compound is administered. In preferred embodiments of this invention, the carrier is a solid carrier. Suitable pharmaceutical carriers include those described in Remington: The Science and Practice of Pharmacy, 21st Ed., Lippincott Williams & Wilkins (2005).

The term "dosage form," as used herein, is the form in which the dose is to be administered to the subject or patient. The drug is generally administered as part of a formulation that includes nonmedical agents. The dosage form has unique physical and pharmaceutical characteristics. Dosage forms, for example, may be solid, liquid or gaseous. "Dosage forms" may include for example, a capsule, tablet, caplet, gel caplet (gelcap), syrup, a liquid composition, a powder, a concentrated powder, a concentrated powder admixed with a liquid, a chewable form, a swallowable form, a dissolvable form, an effervescent, a granulated form, and an oral liquid solution. In a specific embodiment, the dosage form is a solid dosage form, and more specifically, comprises a tablet or capsule.

As used herein, the term "inert" refer to any inactive ingredient of a described composition. The definition of "inactive ingredient" as used herein follows that of the U.S. Food and Drug Administration, as defined in 21 C.F.R. 201.3(b)(8), which is any component of a drug product other than the active ingredient.

Methods and Uses

Methods of the present invention include the use of a transposon inhibitor to treat disorders in a subject. As used herein, the term "disorder" may be used interchangeably with "condition" or "disease".

The terms "treating," "treatment," and "treat" cover therapeutic methods directed to a disease-state in a subject and include: (i) preventing the disease-state from occurring, in particular, when the subject is predisposed to the disease-state but has not yet been diagnosed as having it; (ii) inhibiting the disease-state, e.g., arresting its development (progression) or delaying its onset; and (iii) relieving the disease-state, e.g., causing regression of the disease state until a desired endpoint is reached. Treating also includes ameliorating a symptom of a disease (e.g., reducing the pain, discomfort, or deficit), wherein such amelioration may be directly affecting the disease (e.g., affecting the disease's cause, transmission, or expression) or not directly affecting the disease.

As used in the present disclosure, the term "effective amount" is interchangeable with "therapeutically effective amount" and means an amount or dose of a compound or composition effective in treating the particular disease, condition, or disorder disclosed herein and thus "treating" includes producing a desired preventative, inhibitory, relieving, or ameliorative effect. In methods of treatment according to the invention, "an effective amount" of at least one compound according to the invention is administered to a subject (e.g., a mammal). An "effective amount" also means an amount or dose of a compound or composition effective to The term "animal" is interchangeable with "subject" and may be an invertebrate, particularly *Drosophila*. An animal may also be a vertebrate, particularly a mammal, and more particularly, a human. An animal also includes a laboratory animal in the context of a clinical trial or screening or activity experiment.

As used herein, a "control animal" or a "normal animal" is an animal that is of the same species as, and otherwise comparable to (e.g., similar age, sex), the animal that is trained under conditions sufficient to induce transcription-dependent memory formation in that animal.

By "enhance," "enhancing" or "enhancement" is meant the ability to potentiate, increase, improve or make greater or better, relative to normal, a biochemical or physiological action or effect. For example, enhancing long term memory formation refers to the ability to potentiate or increase long term memory formation in an animal relative to the normal long term memory formation of the animal or controls. As a result, long term memory acquisition is faster or better retained. Enhancing performance of a cognitive task refers to the ability to potentiate or improve performance of a specified cognitive task by an animal relative to the normal performance of the cognitive task by the animal or controls.

As used herein, a "control subject" or a "normal subject" is an animal that is of the same species as, and otherwise comparable to (e.g., similar age, sex), the animal that is being tested, e.g., a test subject with a neurodegenerative disorder being measured for the expression level of at least one transposon in a biological sample from the test subject.

The terms "inhibit," "down-regulate," or "reduce" include decreasing expression of a gene, or level of RNA molecules or equivalent RNA molecules encoding one or more proteins or protein subunits, or activity of one or more gene products, proteins or protein subunits below that observed in the absence of one or more inhibitors, i.e., one or more transposon inhibitors, as defined herein.

Reference will now be made to the embodiments of the present invention, examples of which are illustrated by and described in conjunction with the accompanying drawings and examples. While certain embodiments are described herein, it is understood that the described embodiments are not intended to limit the scope of the invention. On the contrary, the present disclosure is intended to cover alternatives, modifications, and equivalents that can be included within the invention as defined by the appended claims.

Compositions

Compounds, drugs, and agents, including inhibitors, in accordance with the present invention can be administered alone, or alternatively, in the form of pharmaceutical compositions. The compounds (as well as compositions) of the present invention may also be used in the manufacture of a medicament for the therapeutic applications described herein. A pharmaceutical composition of the invention comprises: (a) an effective amount of at least one active agent in accordance with the invention; and (b) a pharmaceutically acceptable excipient.

In particular embodiments, a pharmaceutical composition comprises an apoptosis inhibitor or a transposon inhibitor, as defined herein, or combinations thereof. A pharmaceutical composition may also comprise other active ingredients.

Formulations And Administration

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

Any suitable route of administration may be employed for providing a mammal, especially a human, with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

In some embodiments, the pharmaceutical compositions of the present invention comprise a transposase inhibitor as an active ingredient (or a pharmaceutically acceptable salt thereof), and may also contain a pharmaceutically acceptable carrier and optionally other therapeutic ingredients.

In other embodiments, the pharmaceutical compositions of the present invention comprise an apoptosis inhibitor as an active ingredient (or a pharmaceutically acceptable salt thereof), and may also contain a pharmaceutically acceptable carrier and optionally other therapeutic ingredients.

Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. A compound (transposon inhibitor) of the present invention is typically formulated into pharmaceutical dosage forms to provide an easily controllable and appropriate dosage of the drug.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are typically prepared by incorporating the active compound in the required amount in the appropriate solvent with various of the other ingredients enumerated above, as required, followed by filter sterilization. In the case of sterile powders for the preparation of sterile injectable solutions, common methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Dosages

Useful dosages of inhibitors of the present invention, including transposon inhibitors and apoptosis inhibitors, can be determined by numerous means known in the art, such as comparing their in vitro activity, and in vivo activity in animal models. Methods for the extrapolation of effective dosages in mice, and other animals, to humans are known to the art.

Optimal dosages to be administered in the therapeutic methods of the present invention may be determined by those skilled in the art and will depend on multiple factors, including the particular composition in use, the strength of the preparation, the mode and time of administration, and the advancement of the disease or condition. Additional factors may include characteristics on the subject being treated, such as age, weight, gender, and diet.

In general, however, a suitable dose will be in the range of from about 0.01 to about 100 mg/kg, more specifically from about 0.1 to about 100/mg/kg, such as 10 to about 75 mg/kg of body weight per day, 3 to about 50 mg per kilogram body weight of the recipient per day, 0.5 to 90 mg/kg/day, or 1 to 60 mg/kg/day (or any other value or range of values therein). The compound is conveniently administered in unit dosage form; for example, containing 1 to 1000 mg, conveniently 10 to 750 mg, most conveniently, 50 to 500 mg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of temporally-distinct administrations used according to the compositions and methods of the present invention.

Effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. Such compositions and preparations should contain at least 0.1% of active compound. The percentage of the compositions and preparations may, of course, be varied and may conveniently be between 2 to about 60% of the weight of a given unit dosage form. The amount of active compound in such therapeutically useful composition is such that an effective dosage level will be obtained. An exemplary dose is in the range of from about 0.001 to about 200 mg of active agent per kg of subject's body weight per day, preferably about 0.05 to 100 mg/kg/day, or about 1 to 35 mg/kg/day, or about 0.1 to 10 mg/kg/daily in single or divided dosage units (e.g., BID, TID, QID). For a 70-kg human, an illustrative range for a suitable dosage amount is from 1 to 200 mg/day, or about 5 to 50 mg/day.

Uses and Methods

Monitoring Neuronal Function

The present invention is partly based on the findings that several TEs are highly active in the brain during normal aging in a healthy subject. Accordingly, the present invention provides a method of monitoring neuronal function during aging, comprising measuring expression of at least one transposon in a biological sample from a subject; and determining whether the measured transposon expression exceeds a predetermined level.

Determining the Risk of Age-Related Neuronal Decline and Age-Related Mortality The present invention is also partly based on the findings that premature TE activation leads to progressive age-related neuronal decline and age-related mortality in otherwise normal animals.

Accordingly, in one embodiment, the present invention provides a method of determining the risk of age-related neuronal decline, comprising measuring expression of at least one transposon in a biological sample from a subject; and determining whether the measured transposon expression exceeds a predetermined level, wherein measured transposon expression that exceeds the predetermined level indicates that the subject is at risk of accelerated age-related cognitive decline.

In a second embodiment, the present invention provides a method of determining the risk of age-related mortality, comprising measuring the expression level of at least one transposon in a biological sample from a subject; and determining whether the measured transposon expression exceeds a predetermined level, wherein measured transposon expression that exceeds the predetermined level indicates that the subject is at risk of accelerated age-related mortality.

Transposons

Several studies have reported somatic transposition in early embryonic development and during neurogenesis, suggesting a possible role in the brain (Goodier and Kazazian, Cell 2008, 135, 23-35; 2-5; Muotri et al., Nature 2010, 468, 443-446; Baillie et al., Nature 2011, 479, 534-537; Coufal et al., Proc. Natl. Acad. Sci. USA 2011, 108, 20382-20387). In addition, elevated expression of certain TEs, including LINE, SINE and LTR elements, has been observed in several neurodegenerative disorders and their animal models, suggesting a possible role in the brain (Jeong et al., Clin. Virol. 2009, 47, 136-142; Lathe et al., Mol. Biol. 2009, 392, 813-822; Muotri et al., Nature 2010, 468, 443-446; Coufal et al., Proc. Natl. Acad. Sci. USA, 2011, 108, 20382-20387; Douville et al., Ann. Neurol 2011, 69, 141-151; Keneko et al., Nature 2011, 471, 325-330; Tan et al., Hum. Mol. Genet. 2012, 57-65; Li et al., PLoS One 2012, 7, e44099).

Transposable elements (TEs), or transposons, can be grouped into three groups, or classes, based on their overall organization and mechanism of transposition. See, e.g., Ch. 11, Molecular Biology of the Gene, Watson J. D., et al., $6^{th}$ ed., CSHL Press, NY 2008. These groups comprise; (1) DNA transposons (also referred to as DNA elements, or DNA mobile elements); (2) Long terminal repeat (LTR) retrotransposons (also referred to as LTR transposons, LTR elements, and virus-like (retro)transposons; and (3) non-LTR retrotransposons (also referred to as non-viral (retro)transposons, or poly(A) retrotransposons).

Collectively, LTR elements and non-LTR elements comprise retroelements, which are able to amplify to new locations in the genome through an RNA intermediate. Retroelements represent approximately 40% of the human genome, while DNA transposons account for about 2-3%. See, e.g., Lander et al., 2001, Nature 409, 860-921; Hua-Van et al., 2011, Biol. Dir. 6, 19. These three groups will now be described in more detail.

DNA Transposons

DNA transposons have sequences that function as recombination sites. These sites are at the two ends of the DNA element, are organized as inverted-repeat sequences, and carry the recognition sequences for recombination. DNA transposons can also carry genes encoding proteins responsible for transposition (usually called transposases, or sometimes, integrases). DNA transposons can exist as both autonomous elements (carrying a pair of inverted terminal repeats and a transposases gene), which have everything needed to promote their own transposition; and nonautonomous elements (carrying only the inverted terminal repeats), which depend on a "helper" transposon to donate the transposases needed for transposition.

DNA elements can move by non-replicative and replicative mechanisms. The non-replicative recombination pathway is called cut-and-past transposition, because it involves excision of the transposon from its initial location in the host DNA, followed by integration of the excised transposon into a new DNA site. The replicative recombination pathway involves the duplication of the element DNA during each round of transposition.

LTR Retrotransposons

LTR retrotransposons, which include retroviruses, make up a significant fraction of the typical mammalian genome, comprising about 8% of the human genome and 10% of the mouse genome. (Lander et al., 2001, Nature 409, 860-921; Waterson et al., 2002, Nature 420, 520-562.) LTR elements include retrotransposons, endogenous retroviruses (ERVs), and repeat elements with HERV origins, such as SINE-R. LTR retrotransposons include two LTR sequences that flank a region encoding two enzymes: integrase and reverse transcriptase (RT).

ERVs include human endogenous retroviruses (HERVs), the remnants of ancient germ-cell infections. While most HERV proviruses have undergone extensive deletions and mutations, some have retained ORFS coding for functional proteins, including and the glycosylated env protein. The env gene confers the potential for LTR elements to spread between cells and individuals. Indeed, all three open reading frames (pol, gag, and env) have been identified in humans, and evidence suggests that ERVs are active in the germline. See, e.g., Wang et al., 2010, Genome Res. 20, 19-27. Moreover, a few families, including the HERV-K (HML-2) group, have been shown to form viral particles, and an apparently intact provirus has recently been discovered in a small fraction of the human population. See, e.g., Bannert and Kurth, 2006, Proc. Natl. Acad. USA 101, 14572-14579.

LTR retrotransposons insert into new sites in the genome using the same steps of DNA cleavage and DNA strand-transfer observed in DNA transposons. In contrast to DNA transposons, however, recombination of LTR retrotransposons involves an RNA intermediate. LTR retrotransposons

Non-LTR Retrotransposons

A non-LTR element terminates in 5' and 3' untranslated region (UTR) sequences and encodes two enzymes: ORF1, an RNA-binding enzyme; and ORF2, an enzyme having both reverse transcriptase and endonuclease activities. Like LTR retrotransposons, non-LTR retrotransposons also move via an RNA intermediate. But the mechanism for mobilization of non-LTR retrotransposons—which is target-site primed reverse transcription (or "reverse splicing")—is different from the mechanism used for transposition by LTR retroelements.

Non-LTR retrotransposons include nonautonomous elements, such as Alu elements and SVA (SINE-VNTR-Alu) elements. Non-LTR transposons also include autonomous elements, such as LINEs ("long interspersed nuclear elements). LINEs are abundant in the vertebrate genome, comprising about 20% of the human genome. LINE-like elements, such as R1 and R2, are also present in invertebrates such as *Drosophila*.

A well-studied LINE in humans is L1, which so far appears to be the only active autonomous retrotransposon in the human genome. However, LINEs such as L1 can donate the proteins necessary to reverse-transcribe and integrate another related class of repetitive sequences: the nonautonomous poly (A) retrotransposons known as SINEs ("short interspersed nuclear elements). Genome sequences reveal the presence of huge numbers of SINEs, which are typically between 100 and 400 bp in length. The Alu sequence is an example of a widespread SINE in the human genome. The nonautonomous Alu elements, as well as processed pseudogenes, are retrotransposed in trans by the L1 retrotransposition proteins. Indeed, greater than 30% of the human genome has been generated through retrotransposition of LINE elements and other RNA species by the LINE reverse transcriptase. (Cordaux and Batzer, 2009, Nat. Rev. Genet. 10, 691-703). Retrotransposition is ongoing in human populations as indicated by de novo L1, Alu, and SVA insertions associated with disease and by the large number of polymorphic insertions, many of which are at a low allele frequency in human genomes. See, e.g., Pickeral et al., 2000, Genome Res. 21, 985-990; Beck et al., 2010, Cell 141, 1159-1170; Huang et al., 2010, Cell 141, 1171-1182; Hormozdiari et al., 2011, Genome Res. 21, 840-849.

Delaying Age-Related Neuronal Decline and Age-Related Mortality

The present invention is also based on the discovery that selectively disrupting somatic TE control in *Drosophila* accelerates the age-dependent increase in TE transcripts (R2 and gypsy) and ENV protein. The R2 and gypsy transcript levels in 2-4 day old accelerated animals are comparable to that seen in ~28 day wild-type animals. In addition, TE activation is correlated with age-dependent neuronal decline, as indicated by a deficit in long-term memory. The present invention is also based on the discovery that genetic manipulations—using an RNAi transgene to target loki, the *Dorosophila* ortholog of chk2 exclusively in neurons in wild-type animals significant delays age-dependent mortality and also yields a modest but significant delay in age-dependent memory impairment.

Hence the present invention includes the use of a transposase inhibitor or an apoptosis inhibitor to delay age-related neuronal decline or age-dependent mortality.

Accordingly, in one embodiment, the present invention includes steps and methods of delaying age-related neuronal decline, comprising administering to a subject in need of such treatment an effective amount of a transposon inhibitor.

Accordingly, in another embodiment, the present invention includes steps and methods for delaying age-related neuronal decline and age-dependent mortality, comprising administering to administering to a subject in need of such treatment an effective amount of an apoptosis inhibitor

Transposon Inhibitors

In some embodiments, the methods of the present invention include administering to a subject an effective amount of a transposon inhibitor. In a general aspect, a transposon inhibitor can be an inhibitor of TE expression, such as an inhibitor of transcription of an LTR transposon. In another aspect, a transposon inhibitor can be an inhibitor of TE mobilization, for example, prevent a TE from inserting into a new position in the genome.

In some embodiments, a transposon inhibitors include an inhibitor of a protein encoded by a transposon. More particularly, the protein encoded by the transposon can be a transposase; an integrase; a reverse transcriptase; an endonuclease; a protein encoded by gag, pol, or env; an enzyme encoded by ORF1 of a non-LTR retrotransposon, or an enzyme encoded by ORF2 of a non-LTR transposon.

Transposon inhibitors also include, but are not limited to, anti-retroviral drugs (such as AZT, abacavir, etravirine, or raltegravir); compounds that decrease TE RNA stability; inhibitors of reverse transcription, including nucleoside analog inhibitors (NRTIs) such as ddl, ddC, and stavudine, nucleotide analog inhibitors (NtRTIs) such as tenofovir and adeforvir, and non-nucleoside inhibitors (NNRTIs) such as nevirapine and efavirenz; inhibitors of transposase or integrase activity, inhibitors of endonuclease activity, and stimulators of DNA repair machinery, such as doxorubicin and phleomycin.

Furthermore, a transposon inhibitor can include: a zinc-finger protein ("zinc finger") that targets a transposon promoter region; a repressor that inhibits a transposon; an innate antiretroviral resistance factor, such as cAPOBEC3A or APOBEC3B, two members of the APOBEC3 family in humans—which can enter the nucleus and specifically inhibit both LINE-1 and Alu retrotransposition (see, e.g., Bogerd et al., 2006, Proc. Natl. Acad. Sci. USA 103, 8780-8785). Transposon inhibitors can also include small interfering RNAs (siRNAs), short hairpin RNA (shRNAs), morpholinos, and antisense oligonucleotides directed to TE transcripts; and inhibitors of post-translational processing or proteolysis of a transposon-encoded protein, such as the Env protein encoded by some LTR retrotransposons. They also include enzymes or repressors that inhibit TEs, for example, an enzyme that inhibits L1 (such as the protein APOBEC3G) or a repressor that inhibits L1 (such as MePC2 or Sox2).

Transposon inhibitors also include compounds that block transmission of a retroviral particles. For example, they may block binding of env-containing transposon particles to the corresponding receptor for the Env protein.

More generally, transposon inhibitors include compounds that prevent the spread of TEs between cells, i.e., that block intercellular transmission of transposon genetic material or protein. For example, inhibitors may be directed to the formation, transport, and movement of transposon RNAs in exosomes. Exosomes are formed by inward budding of late endosomes, producing multivesicular bodies (MVBs), and are released into the environment by fusion of the MVBs with the plasma membranes. Moreover, exosomes released from cells can contain messenger RNA (mRNA) and microRNA (miRNA) and can shuttle such RNAs and proteins from one cell to another. Exosomes can therefore be transported between different cells and influence physiological pathways in the recipient cells. See, e.g., Bang and Thum, 2012, Int. J. Biochem. Cell Biol. 10, 2060-2064.

Transposon inhibitors also include inhibitors of cellular receptors of endogenous retrovirus (ERV) movement, including, but not limited to, ephrins and ephrin receptors, including members of the Ephrin A family. (Stoye, *Nat. Rev. Microbiol.* 2012, 10, 395-406; Dewannieux et al., *PLoS Pathog.* 2011, 10, e1002309;

Apoptosis Inhibitors

As defined herein, an "apoptosis inhibitor" is a compound, agent, or drug that prevents or inhibits apoptosis, i.e., programmed cell death. As used herein, "apoptosis" refers to the art recognized use of the term for an active process of programmed cell death characterized by morphological changes in the cell. More particularly, apoptosis is a genetically programmed cellular event characterized by well-defined morphological features that include as cell shrinkage, chromatin condensation, nuclear fragmentation, and membrane blebbing. (Kerr et al., *Br. J. Cancer* 1972, 26, 239-257; Wyllie et al., *Int. Rev. Cytol.* 1980, 68, 251-306. It plays an important role in normal tissue development and homeostasis, and defects in the apoptotic program are thought to contribute to a wide range of human disorders ranging from neurodegenerative and autoimmunity disorders to neoplasms. (Thompson, *Science* 1995, 267, 1456-1462; Mullauer et al., *Mutat. Res.* 2001, 488, 211-231).

One group of proteins that plays a key role in apoptosis is a family of cysteine proteases, termed caspases, which appear to be required for most pathways of apoptosis. Creagh & Martin (2001) Biochem. Soc. Trans, 29, 696-701; Dales et al. (2001) Leuk. Lymphoma, 41, 247-253. Caspases trigger apoptosis in response to apoptotic stimuli by cleaving various cellular proteins, which results in classic manifestations of apoptosis, including cell shrinkage, membrane blebbing and DNA fragmentation. Chang & Yang (2000) Microbiol. Mol. Biol. Rev., 64, 821-846.

Pro-apoptotic proteins, such as Bax or Bak, also play a key role in the apoptotic pathway by releasing caspase-activating molecules, such as mitochondrial cytochrome c, thereby promoting cell death through apoptosis. Martinou & Green (2001) Nat. Rev. Mol. Cell. Biol., 2, 63-67; Zou et al. (1997) Cell, 90, 405-413. Anti-apoptotic proteins, such as Bcl-2, promote cell survival by antagonizing the activity of the pro-apoptotic proteins, Bax and Bak. Tsujimoto (1998) Genes Cells, 3, 697-707; Kroemer (1997) Nature Med., 3, 614-620. The ratio of Bax:Bcl-2 is thought to be one way in which cell fate is determined; an excess of Bax promotes apoptosis and an excess of Bcl-2 promotes cell survival. Salomons et al. (1997) Int. J. Cancer, 71, 959-965; Wallace-Brodeur & Lowe (1999) Cell Mol. Life Sci., 55, 64-75.

Another key protein involved in apoptosis is that encoded by the tumor suppressor gene p53. This protein is a transcription factor that regulates cell growth and induces apoptosis in cells that are damaged and genetically unstable, presumably through up-regulation of Bax. Bold et al. (1997) Surgical Oncology, 6, 133-142; Ronen et al., 1996; Schuler & Green (2001) Biochem. Soc. Trans., 29, 684-688; Ryan et al. (2001) Curr. Opin. Cell Biol., 13, 332-337; Zornig et al. (2001) Biochem. Biophys. Acta, 1551, F1-F37.

In accordance with the present invention, an apoptosis inhibitor can prevent programmed cell death by multiple mechanisms. These include, for example, antagonists directed to pro-apoptotic proteins such as a caspase, Bak, and Bax, and agonists directed to anti-apoptotic proteins such as Bcl-1. An apoptosis inhibitor also include stimulators of the DNA repair machinery, as well as endogenous inhibitors of apoptosis, such as those in human IAP (Inhibitor of Apoptosis) family, whose members include Cp-IAP, Op-IAP, XIAP, c-IAP1, c-IAP2, NAIP, and surviving.

Other apoptosis inhibitors are known in the art. See, e.g. U.S. Pat. No. 8,242,122, WO/1999/025346, US20110028491, In a specific embodiment, the apoptosis inhibitor is an inhibitor of a protein that mediates DNA damage-induced apoptosis, such as an inhibitor of a checkpoint kinase, or an inhibitor of Checkpoint kinase 2 specifically.

A pharmaceutical composition may also comprise a mixture of apoptosis inhibiting compounds.

Recombinant Nucleic Acids, Cells, and Transgenic Animals

The present invention is also based on the discovery of a system for detecting de novo transposition events in an aging animal, including in the adult brain. Accordingly, the present invention a recombinant nucleic acid sequence for detecting de novo TE integration events, comprising a promoter region; a reporter gene operably linked to the promoter; and a fragment inserted between the promoter and reporter gene, wherein the fragment comprises binding sites that are necessary and sufficient to attract de novo TE insertions, and does not itself does not disrupt expression of the reporter gene. In a specific aspect, the reporter gene encodes an expression disrupter, which can include GAL80. In another aspect, the fragment is an ovo regulatory region containing multiple Ovo binding sites.

The present invention also include a cell comprising any of the disclosed recombinant nucleic acid sequences. Such a cell may also include a second recombinant nucleic acid sequence, comprising a second promoter region operably linked to a second reporter gene, wherein expression of the second reporter gene is blocked by the expression disruptor. In a particular aspect, expression of the second reporter gene is mediated by GAL4. The invention also includes a transgenic animal, including a transgenic vertebrate or transgenic *Drosophila*, comprising any of the recombinant nucleic sequences herein (or cell that contains any of them).

EXAMPLES

The present disclosure will be further illustrated by the following non-limiting Examples. These Examples are understood to be exemplary only, and they are not to be construed as limiting the scope of the invention as defined by the appended claims.

Methods

Fly Stocks

The wild type flies utilized in this study were w1118 (isoCJ1), a Canton-S derivative 21. The dAgo2 mutants and UAS::dAgo2 transgenic strains were backcrossed to the above wild type strain for at least five generations. Flies were cultured in standard fly food and laboratory room temperature (22.5° C.).

The "gypsy-TRAP" transgenic flies were made by cloning a ~500 bp Ovo binding site (Labrador et al., *Genetics*, 2008, 180, 1367-1378) into the NotI site between Tubulin promoter and GAL80 gene in the Tubp-GAL80 in pCaSpeR4 plasmid. The resulting construct was injected into w1118 (isoCJ1) recipient embryos and transformant lines were isolated by standard procedures at the BestGene, Inc. The mutated "gypsy-TRAP" transgenic flies were made by injecting a similar construct bearing mutations in Ovo binding sites (Labrador et al., *Genetics*, 2008, 180, 1367-1378). The MB247, Repo and Elav-Gal4 lines are as reported previously.

Behavioral Assays

Aversive Pavlovian olfactory task was performed by training flies in a T-maze apparatus using a Pavlovian conditioning paradigm. More particularly, proximately 50-100 flies were loaded into an electrifiable training grid. For a single training session, flies were exposed sequentially to one odor (the conditioned stimulus, CS+), which was paired with a 60-volt electric shock and then a second odor (the unconditioned stimulus, CS−) without shock. Two minutes after this training session, the flies were tested and allowed to choose between the two odors. A half performance index was calculated by dividing the number of flies that chose correctly, minus the flies that chose incorrectly by the total number of flies in the experiment. The same protocol was then performed with another group of 50-100 flies and reciprocal odor presentation. The final PI was calculated by averaging both reciprocal half PIs.

The long-term-memory (LTM) experiment was an adaptation of this training protocol. Flies were subjected to ten such training sessions in robotic trainers spaced out with a 15-minute rest interval between each. Flies then were transferred into food vials and incubated at 18° C. until being tested 24 hours after the training. All genotypes were trained and tested in parallel, and rotated between all the robotic trainers to ensure a balanced experiment. Odor pairs and concentrations used for these behavior paradigms are: 3-Octanol ($1.5 \times 10^{-3}$ v/v) and 4-Methylcyclohexanol ($1 \times 10^{-3}$ v/v), or, 3-Octanol ($1.5 \times 10^{-3}$ v/v) and Benzaldehyde ($0.5 \times 10^{-3}$ v/v). Pure odors were purchased from Sigma and delivered as the stated concentrations with air flow at 750 ml/min. In all cases, behavior experiments within a figure were performed in parallel. Behavioral data are normally distributed and are shown as means±SEM. One-Way ANOVA and post-hoc analyses were performed.

Lifespan

Lifespan were measured with ~50-150 animals/genotype. Equal numbers of male and female flies were used for each genotype. Survival analyses were performed with the Kaplan-Meier Method. Log-rank test and Gehan-Breslow-Wilcoxon test were used to compare survival curves. Pairwise comparisons were made with Bonferroni corrections.

QPCR

The QPCR was performed according to the assay manual. In brief, massive numbers of fly heads were collected for each genotype and total RNA was purified with Trizol (Invitrogen) and treated by DNaseI (Promega). Total RNA concentrations were determined using a NanoDrop ND-1000 spectrophotometer. For the reverse transcription (RT) reaction, each 20 μl RT reaction was performed with 2 μg total RNA using the High capacity RNA-tocDNA kit (Applied Biosystems). The QPCR reactions for each assay were carried out in duplicate, and each 20 μl reaction mixture included 1 μl previous RT products. The QPCR reaction was carried out and analyzed in an Applied Biosystems 7900HT Fast Real-Time PCR System in 96-well plates at 95° C. for 10 min, followed by 40 cycles of 95° C. for 15 sec and 60° C. for 1 min. Linearity tests were performed on all custom designed primers and probes to ensure linearity.

Custom TaqMan Probes

All TaqMan® Gene Expression Assays (Applied Biosystems) utilized the FAM Reporter and MGB Quencher. TaqMan® probes for each transcript were designed following the vendor's custom assay design service manual. The customized gene-specific Taqman probes and inventoried Taqman probes had the following sequences and Assay IDs:

R1-ORF2 (Assay ID AID1TD0, FBgn0003908):
SEQ ID NO: 1
probe: 5'-ACATACGCCATAATCTG-3'

Blood-ORF2 (assay ID AIFARJ8, FBgn0000199)
SEQ ID NO: 2
Probe: 5'-TCGGTGCATAACTTAGTTAGTTCA-3'

GypsyORF2 (Assay ID AI5IO6V, FBgn0001167)
SEQ ID NO: 3
Probe: 5'-AAGCATTTGTGTTTGATTTC-3'

Gypsy4-ORF2 (AID1TGU, FBgn0063433)
SEQ ID NO: 4
Probe: 5'-CCCGATCTGGGTTGTC-3'

ZAM-ORF2 (Assay IDAICSVAM, FBgn0023131)
SEQ ID NO: 5
Probe: 5'-CCCCATGATTAGTCTTTACTG-3'

1731-ORF2 (Assay ID AICSU7S, FBgn0000007)
SEQ ID NO: 6
Probe: 5'-AAGCTGAAGACTGATTTATG-3'

297-ORF2 (Assay ID AI7OLJB, FBgn0000005)
SEQ ID NO: 7
Probe: 5'-TTGATCAAACATACAAATTAATTAC-3'

R25' (Assay ID AJ0IV12, FBgn0003909)
SEQ ID NO: 8
Probe: 5'-GAATGCCATTCCAAATGGAGAGCCC-3'

R23' (Assay ID AJY9XVU, FBgn0003909)
SEQ ID NO: 9
Probe: 5'-TAGAAAAATATTGGGCGAACAAGTT-3'

DBV (Assay ID AIV13YJ)
SEQ ID NO: 10
Probe: 5'-CCTATTAGTGATCCGCTCGCG-3'

DTRV (Assay ID AIS07L3)
SEQ ID NO: 11
Probe: 5'-CTTCGATCCGAGGTATGC-3'

DAV (Assay ID AIX00AZ)
SEQ ID NO: 12
Probe: 5'-AAGGTAGTAGGTTACATTTGTC-3'

Sigma V (Assay ID AIWR14R)
SEQ ID NO: 13
Probe: 5'-CCGTAGTCCGATGGTTCC-3'

Nora V (Assay ID AIQJA9N)
SEQ ID NO: 14
Probe: 5'-CTGAGGCTTCTCTTGTTTAAT-3'

DCV (Assay ID AIPAC3F)
SEQ ID NO: 15
Probe: 5'-TTGTCGACGCAATTCTT-3'

DXV (Assay ID AIRR9FV)
SEQ ID NO: 16
Probe: 5'-TCATAGATGATGTCAAATTT-3'

ANV (Assay ID AIT95SB)

-continued

Probe: 5'-CAGACAATTTCTCAGAATCAT-3'  SEQ ID NO: 17

Act5C (Assay ID Dm02361909_s1)

Loki (Assay ID Dm01811114_g1)

Ago2 (Assay ID Dm01805432_g1 and Dm01805433_g1)

Dcr-2 (Assay ID Dm01821537_g1 and Dm01821540_g1)

Western Blots

Approximately 15 adult fly heads per sample were homogenized in 20 ul Nupage@ sample loading buffer, heated to 95° C. for 5 min and 10 µl loaded onto Nupage@ 4-12% Bis-Tris gels, then transferred to PVDF membrane (Invitrogen) and blotted by standard protocols.

Primary antibodies used were anti-tubulin (1:10,000, E7, Developmental Studies Hybridoma Bank), anti-ENV (1:5000). The WesternBreeze® Chemiluminescent Kit—Anti-Mouse system was used to visualize the blotted bands on films.

Bleach Treatment of Embryos

In order to remove virus infection in fly stocks, 2 hr embryos from wild type controls and dAgo2 mutants were collected and treated with 50% bleach 2 times for 20 minutes each. Treated embryos were then grown in a virus free clean room equipped with UV lamps to sterilize surfaces. Expanded fly stocks after bleach treatment are proven to be virus-free. All strains also were grown on a rotating set of 6 antibiotics.

Immunohistochemistry and GFP Imaging

Dissection, fixation, immunolabeling and confocal imaging acquisition were performed as previously described (Qin, et al., Curr. Biol. 2012, 22, 608-614). Ascites containing anti-gypsy ENV monoclonal antibody (mAb) was prepared from the anti-gypsy ENV 7B3 hybridoma cell line (Chen at al., PLoS Comput. Biol. 2008, 4, e10000026). A 1:100 dilution of ENV primary mAb and a 1:200 dilution of secondary antibody of Cy3-conjugated goat anti-mouse IgG were used. 2 µM DilC18(5)-DS lipophilic dye solution (Molecular Probes) was used to label cell membranes throughout the brain as counterstaining. For Env immunolabeling, multiple brains of each genotype and age were imaged. Representative images are shown in the Figures. Total numbers imaged for wild type were: 6 (0-4 day), 14 (14 day), 16 (21-28 day), 4 (70 day). For dAgo2$^{414}$, total number imaged were: 8 (14 day), 7 (21-28 day). For dAgo2$^{-51b}$, total number imaged were: 5 (0-4 day), 6 (14 day), 6 (21-28 day), 3 (70 day). For dAgo2$^{454}$, total number imaged were 9 (0-4 day), 13 (14 day), 6 (21-28 day).

Nested PCR

DNA was extracted from ~300 fly heads of the indicated ages. Standard PCR was performed in nested fashion with the first round of PCR utilizing primer 1 and 3 followed by a second round of PCR with primer 2 and 4. Primer sequences are listed below. Nested PCR was then run on 0.9% agarose gel (Sigma) and the product size was estimated according to 1 kb plus DNA ladder (Invitrogen). The PCR product was then gel purified using illustra GFX PCR DNA and Gel Band Purification Kit from GE Healthcare. The fragment was cloned using the TOPO TA Cloning Kit for sequencing from Invitrogen and sequenced by ELIM BIOPHARM using the Sanger sequencing method. MacVector was used to display sequencing results.

| Primers | | |
|---|---|---|
| Primer 1 - CAACTCTGCACCCACGACTA | SEQ ID NO: 18 |
| Primer 3 - CAGCGGAAAGCTGACACTTC | SEQ ID NO: 19 |
| Primer 2 - CACACACCCATGGAATTGAA | SEQ ID NO: 20 |
| Primer 4 - GGCTCATTGCCGTTAAACAT | SEQ ID NO: 21 |

Statistical Testing

Behavioral data from the Pavlovian memory task are normally distributed (Tully et al., Cell, 1994, 79, 35-47) and are shown in all Figures as means±SEM. For these data, one-Way ANOVA and post-hoc analyses were performed. For the lifespan curves, survival analyses were performed with the Kaplan-Meier Method. Log-rank test and Gehan-Breslow-Wilcoxon test were used to compare survival curves. Pairwise comparisons were made with Bonferroni corrections.

Example 1

Age-Dependent TE Expression and

TE expression was first examined in Drosophila, where it is feasible to manipulate the TE control mechanisms and to measure physiological effects on the nervous system. Quantitative Real-Time PCR (QPCR) was used to measure levels of several TE transcripts in head tissues during normal aging by comparing transcript levels from 2-4-day old adult wild-type flies with that of ~14, ~21 and ~28-day old counterparts. Surprisingly, transcripts from R2 (a LINE-like element) and gypsy (an LTR element) are dramatically elevated in aged relative to young animals (FIG. 1A). R1, a second LINE-like element also shows elevated expression with age (see below). Although these studies have not exhaustively examined expression of the TE families in the Drosophila genome, the age-dependent expression may impact certain TEs specifically because not see effects were seen on gypsy4 or Zam (data not shown).

Figure 1B:
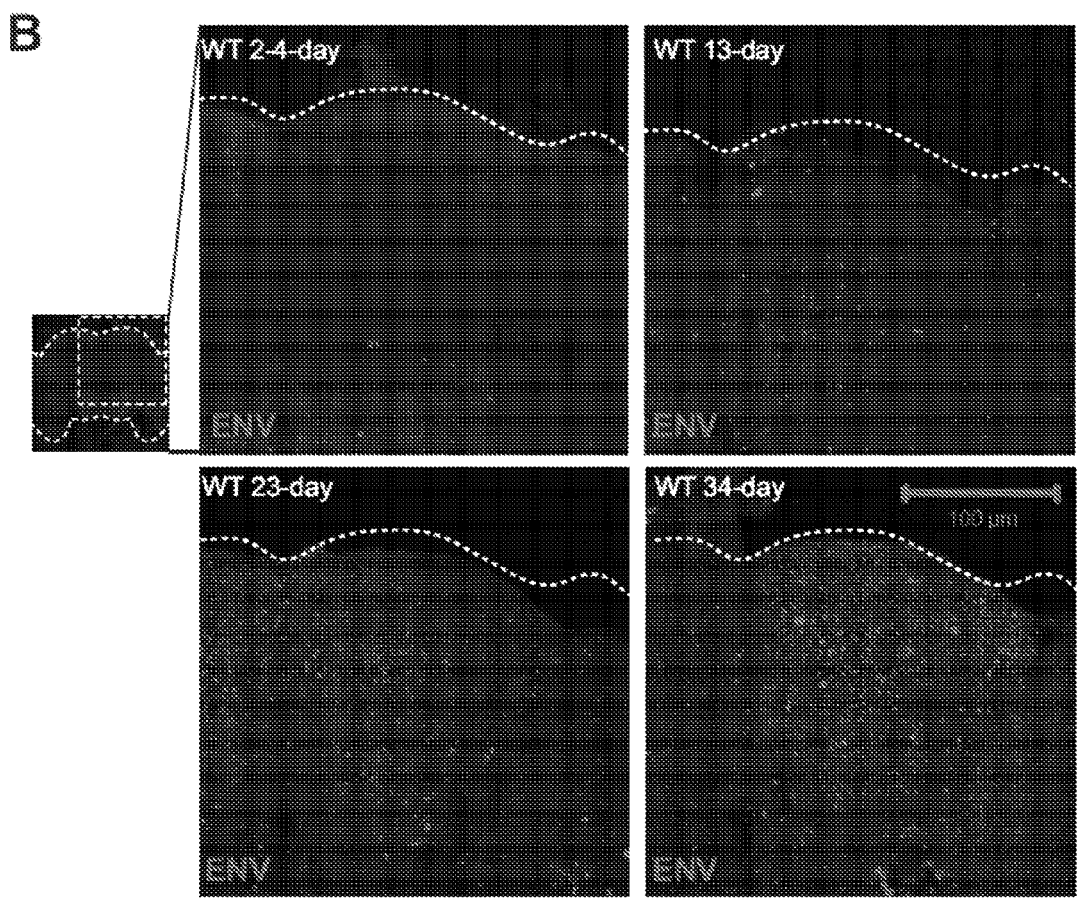
FIG. 1B is a panel of images showing that ENV immunofluorescence is progressively elevated in brains from older animals (13-day, 23-day, 34-day) relative to brains from ~2-4-day old animals (these images were taken under identical confocal settings). ENV labeling is shown as a confocal projection through the central brain. Elevated levels of ENV are seen in aged brains throughout the cortex layer that includes most of the cell bodies as well as in neuropil areas of axons and dendrites (see also individual confocal sections in FIGS. 3B and 6).

In addition to the effects on transcripts from gypsy, R1 and R2, an age-dependent increase in expression of the gypsy membrane glycoprotein ENV was detected, using immunohistochemical staining in whole mount brains (FIG. 1B). The ENV signal is most intense in the cortical regions that contain most of the cell bodies, but also is detected in neuropil, areas containing axons and dendrites (central brain projections shown in FIG. 1B; see also individual confocal sections FIGS. 3B and 8B).

Figure 4:
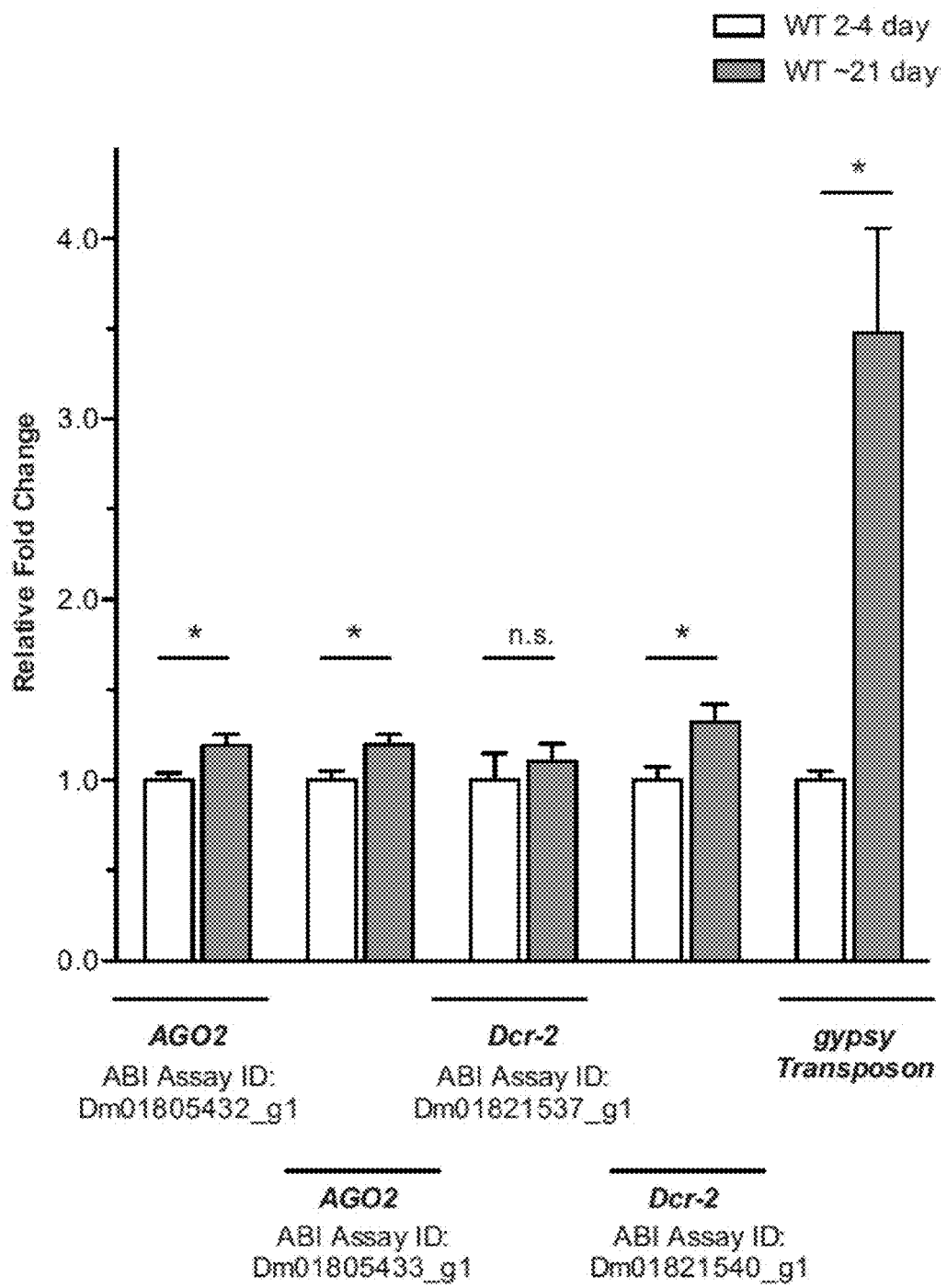
FIG. 4 is a histogram showing expression levels of dAGO2 and Dcr-2 in fly heads from both 2-4 day old (young) animals and ~21 day-old aged animals, as measured by QPCR. A moderate increase (*, $p<0.05$) of dAGO2 expression was observed with two independent dAGO2 Taqman assays tested. A moderate increase (*, $p<0.05$) of Dcr-2 expression was observed with one of two independent Dcr-2 Taqman assays tested.
Figure 5A:
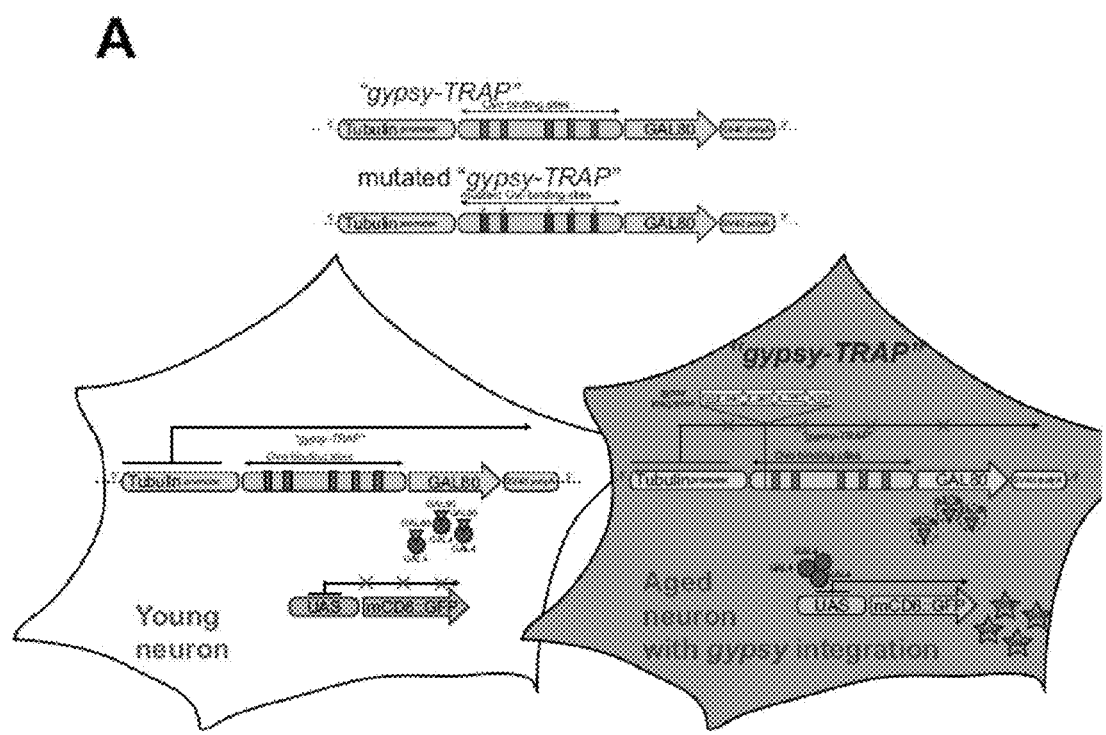

This age-dependent depression of TEs was not due to loss of expression of either Dicer-2 or dAGO2, proteins required for TE silencing in somatic tissues 14 (FIG. 4). To determine if expression of gypsy in older animals is associated with physical transposition, a "gypsy-TRAP" reporter system was designed to detect de novo gypsy integration events. This was accomplished by adapting a reporter system previously established for detecting gypsy integration in the germline (Labrador, et al. Genetics 180, 2008, 108, 1367-1378). This was achieved by expressing GAL80, which is an effective repressor of GAL4, under control of the ubiquitous α-tubulin promoter. In the presence of GAL80 protein, GAL4-mediated expression of GFP is effectively silenced. A ~500 bp fragment from the ovo regulatory region was placed between the promoter and GAL80 in order to attract gypsy insertional mutations (FIG. 5A). This fragment contains 5 Ovo binding sites to which the Ovo protein normally binds in its own regulatory region. In the germline, these Ovo binding sites are necessary and sufficient to attract de novo gypsy insertions (Labrador, et al. *Genetics* 180, 2008, 108, 1367-1378). In the reporter system of the present invention, somatic integration of gypsy downstream of the promoter or within the GAL80 transcription unit disrupts expression of GAL80, permitting activation of GFP by GAL4 (FIG. 2B).

Figure 2:
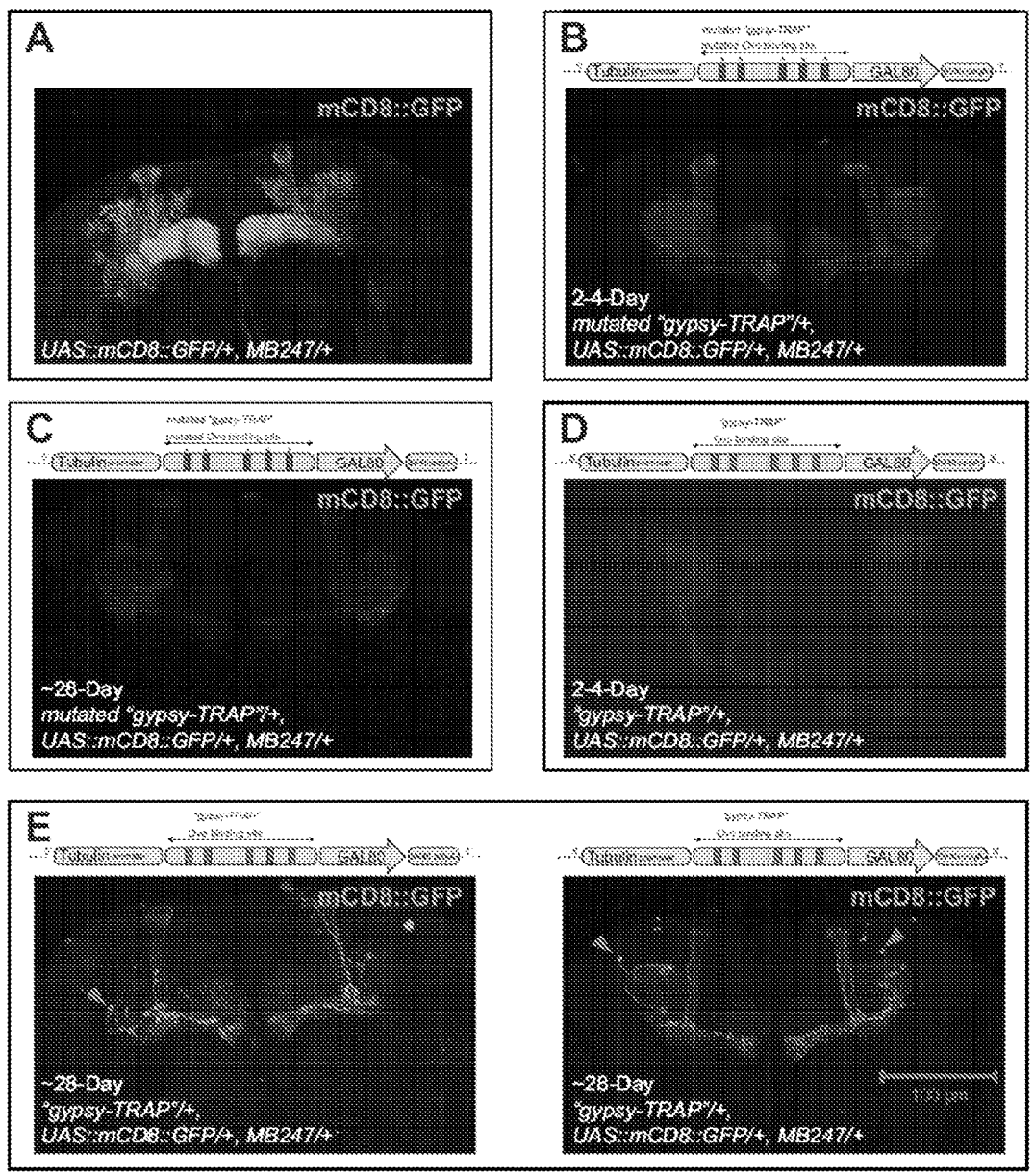
FIG. 2 is a panel of images from screening studies for de novo gypsy integration events in the mushroom body (MB) neurons of *Drosophila* wild-type brain using control and experimental "gypsy-TRAP" reporter systems. A ~500 bp fragment from the ovo regulatory region containing 5 Ovo binding sites is inserted between Tub promoter and GAL80 gene. A mutated "gypsy-TRAP" construct contains mutations that disrupt each of the 5 Ovo binding sites. In the absence of gypsy insertions, GAL80 expression suppresses GAL4, and UAS::mCD8::GFP is not expressed. In the presence of gypsy integration into the "gypsy-TRAP", GAL80 expression is blocked, and UAS::mCD8::GFP is turned on (see FIG. 5). (A) Approximately 800 mushroom body Kenyon cell neurons per brain hemisphere are labeled by MB247-GAL4-driven UAS::mCD8::GFP. (B) An exemplary brain from 2-4-day old mutated "gypsy-TRAP"; UAS::mCD8::GFP/+; MB247/+. No GFP labeled neurons are seen. (C) An exemplary brain from ~28-day old mutated "gypsy-TRAP"; UAS::mCD8::GFP/+; MB247/+. No GFP labeled neurons seen. (D) An exemplary brain from ~2-4-day old "gypsy-TRAP"; UAS::mCD8::GFP/+; MB247/+. No GFP labeled neurons are seen. (E) Exemplary brains from ~28-day old "gypsy-TRAP"; UAS::mCD8::GFP/+; MB247/+. Several GFP-labeled MB neurons seen in each brain. See Table 1 and FIG. 5 for statistical summary and additional exemplary images.
Figure 5B:
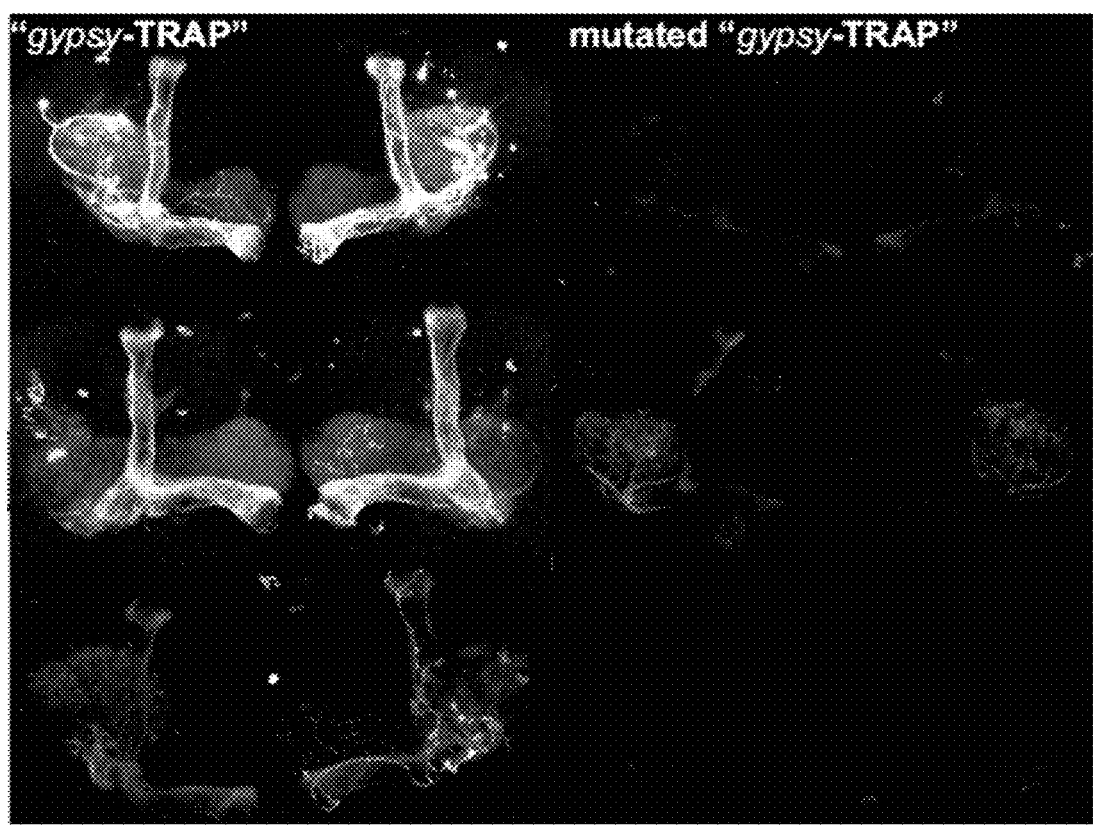
FIG. 5B is an image showing that "gypsy-TRAP" reporter detects de novo integration of gypsy in neurons in aged wild-type animals. As in FIG. 2, the "gypsy-TRAP" reporter was combined with MB247-GAL4 line, and UAS::mCD8::GFP. In brains from aged animals (28-35 day post eclosion) sparsely GFP labeled mushroom body neurons are consistently observed (three examples shown in left panels, see also FIG. 2 and Table 1). As is true in germline, insertion of gypsy into this cassette requires the presence of Ovo binding sites. No labeled neurons are seen with the mutated "gypsy-TRAP" construct in which these sites are mutated (three examples shown in right panels, see also FIG. 2 and Table 1).

This system was used to screen for de novo gypsy integration events in the brain by focusing on neurons of the mushroom body (MB) for which highly specific and strongly expressing GAL4 lines exist. We used the MB247 GAL4 line16, which is known to label about 800 out of ~2000-2500 mushroom body Kenyon cell neurons per brain hemisphere (FIG. 2A). GAL80 expression from "gypsy-TRAP" (Tubp-OvoSite-GAL80) transformant lines is sufficient to silence GFP (FIGS. 2 and 5). In fact, no labeled neurons were observed in 2-4-day old animals containing this construct (0/26 brains from 2-4 day old animals, FIGS. 2B, 2C, 5). However, sparse GFP-labeled MB Kenyon cells were observed at later ages in each of two transformant lines containing "gypsy-TRAP" (Tubp-OvoSite-GAL80), often in multiple neurons (14/39 brains labeled from 28-35 day old animals, FIGS. 2E, 5). This effect of age was statistically significant (Chi-square Analysis, $p<0.01$). The labeling appears to be stochastic because both intra and inter-hemisphere variation was seen.

The accumulation of GFP positive neurons also requires the 5 Ovo binding sites, as is true for gypsy insertions in the germline, because there were no observed GFP-labeled cells in control transformant lines containing a "gypsy-TRAP" with an ovo fragment in which the binding sites are mutated (Tubp-MutatedOvoSite-GAL80) (FIGS. 2B; 5; Chi-square Analysis, $p<0.001$). The results using this reporter system strongly support the conclusion that gypsy not only is expressed in neurons of aging animals, but also is actively mobile in an age dependent manner.

These results from this analysis of mutated and non-mutated "gypsy-TRAP" transgenic lines are summarized in Table 1:

TABLE 1

|  | 2-4-day | ~14-day | ~21-day | 28-35-day |
| --- | --- | --- | --- | --- |
| mutated gypsy "TRAP" | | | | |
| transformant line #1 | 0/15[1] | 0/4 | 0/9 | 0/11 |
| transformant line #2 | 0/8 | 0/2 | — | 0/3 |
| gypsy "TRAP" | | | | |
| transformant line #1 | 0/15 | 0/1 | — | 4/16[2] |
| transformant line #2 | 0/11 | 2/3[1] | 1/6 | 10/23 |

Example 2

Premature TE Activation in Young Animals Leads to Age-Dependent Neuronal Decline and Reduced Life-Span The dAgo2 gene was genetically manipulated to create a situation in which transposons are unleashed prematurely in young animals. In both animals and plants, TE control is mediated by Argonaute proteins guided by small regulatory RNAs (Czech and Hannon, *Nat Rev Genet*, 2011, 12, 19-31). Germline tissues are protected against TEs by the concerted action of Argonaute proteins of the PIWI Glade and their small RNA partners, the piRNAs (Czech et al., *Nat Rev Genet*, 2003, 12, 19-31).

While control of TEs in somatic tissues in *Drosophila* is dependent on dAGO2 guided by endogenous small interfering RNAs, a different Argonaute protein in flies, dAGO1, preferentially loads the microRNAs that target cellular mRNAs, but has no known impact on TEs. Therefore, using dAgo2 mutants creates condition allowing selective disruption of the somatic TE control mechanism. Although dAgo2 mutants have been shown to exhibit elevated TE expression in somatic tissue, the phenotypic consequences of such mutations on aging are not known.

Figure 3A:
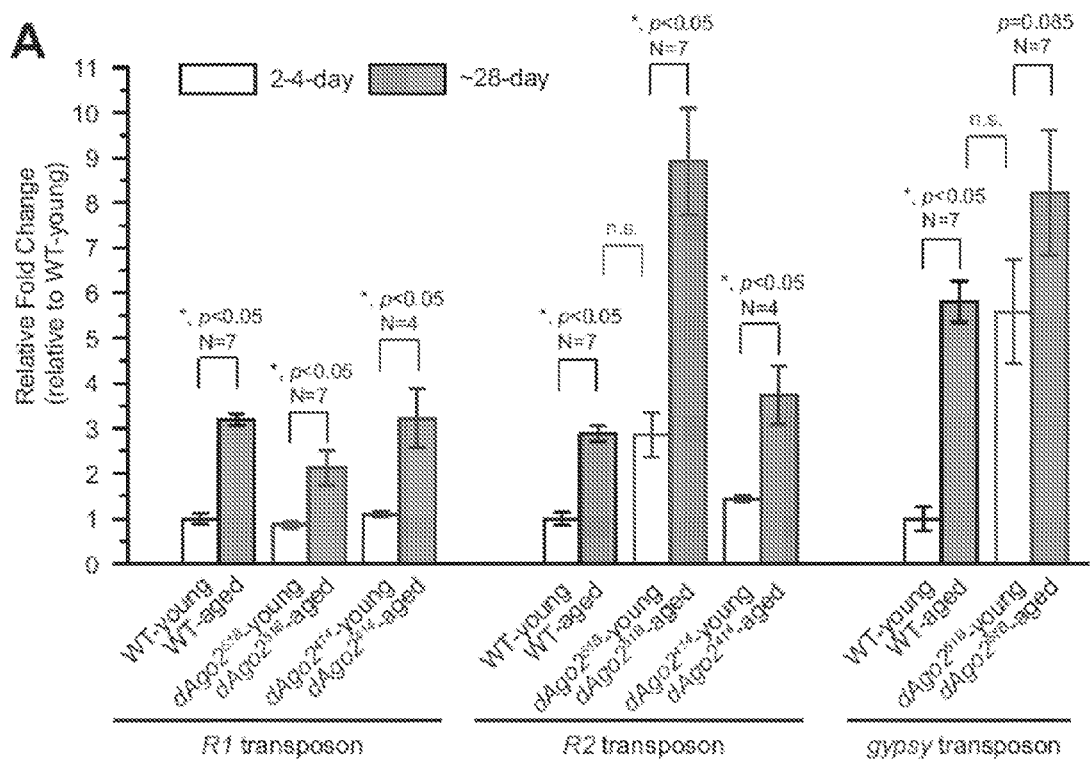
FIG. 3A is a histogram showing that age-dependent TE expression contributes to memory decline and age-dependent mortality. Levels of transcripts of R1, R2 and gypsy were quantified from young (2-4-day) and aged (~28-day) WT and dAgo2 mutant animal heads. Within all genotypes, aged animals have significantly elevated levels of each of the transposon transcripts (R1, R2, and gypsy), compared to young animals (*, $p<0.05$, N=4 for both young and aged dAgo2$^{414}$ groups, N=7 for both young and aged WT and dAgo2$^{51B}$ groups), except for the comparison between young and aged groups within dAgo2$^{51B}$ ($p=0.085$) for gypsy, which also is elevated in young animals. For R2 and gypsy, transcript levels in dAgo2$^{51B}$ young groups are as high as in WT aged groups. ~28-day old dAgo2$^{51B}$ animals exhibit dramatically increased levels of R2 compared to aged WT group (*, $p<0.05$). For R2, the 5' probe set was used in this experiment (see Methods in the Examples Section herein).
Figure 3B:
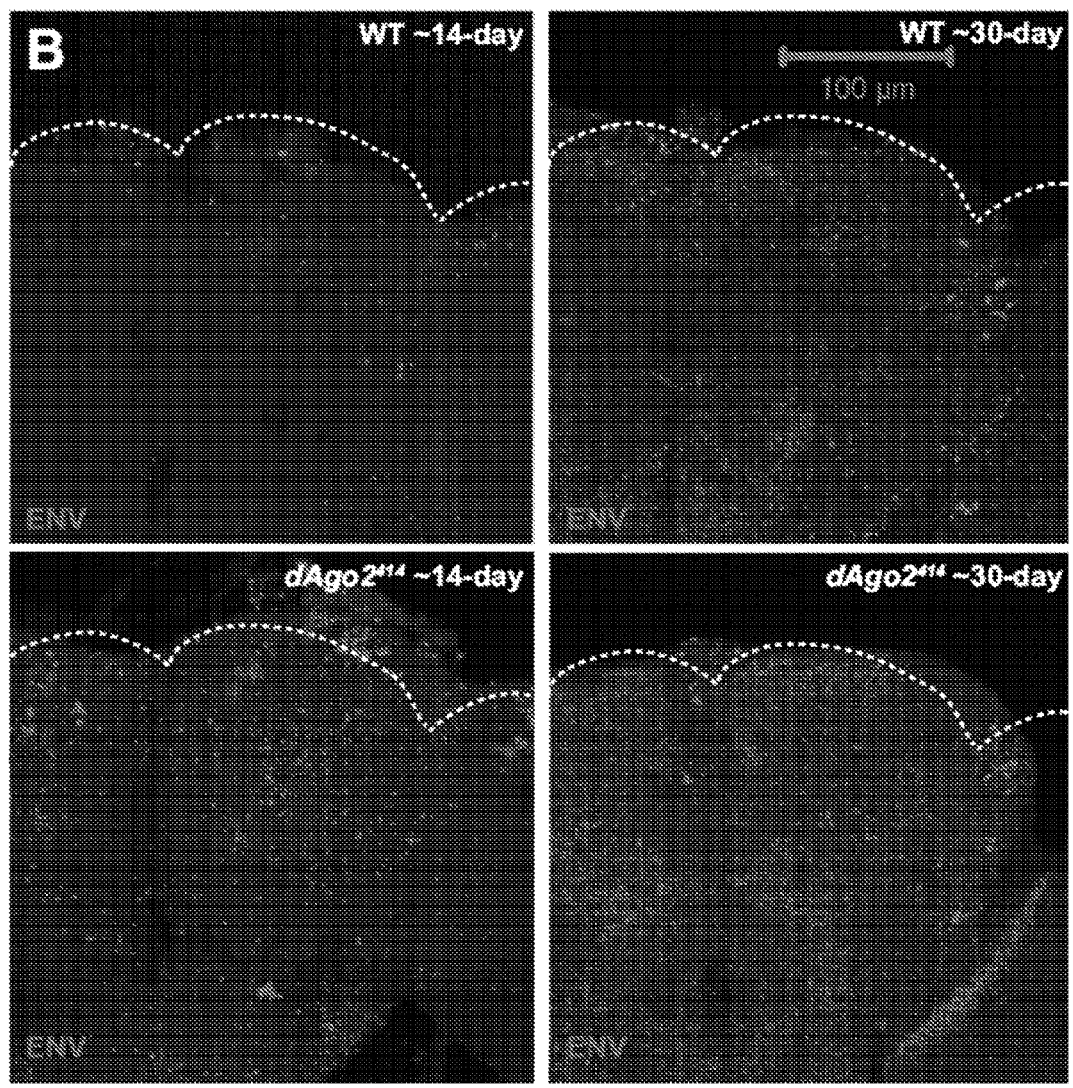
FIG. 3B is a panel of images showing detection of ENV immunoreactivity throughout the cortex layer that includes most of the somata as well as in neuropil (see also FIGS. 1 and 8B). Central projections are shown for whole mount brains. Brains from dAgo2$^{414}$ mutants exhibit higher levels of ENV immunolabeling in ~14-day old and ~30-day old animals, as also is observed with other dAgo2 alleles (See also FIG. 8B).
Figure 3C:
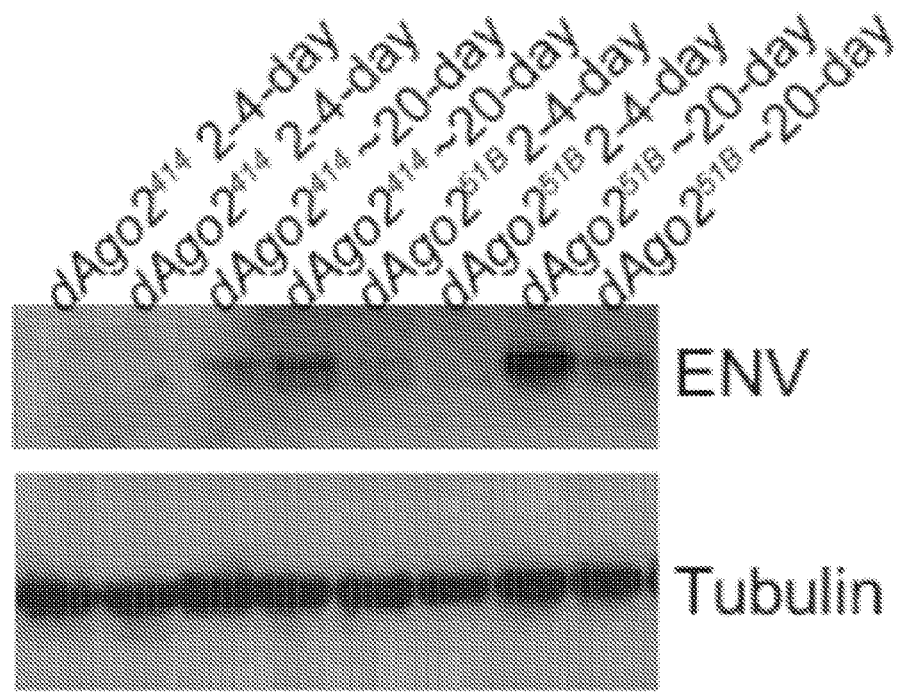
FIG. 3C is an image showing western blot detection of ENV with a monoclonal antibody and age-dependent accumulation in heads from dAgo2 mutant animals (see also FIG. 8A). Levels for dAgo2$^{51B}$ appear increased although somewhat variable.
Figure 6:
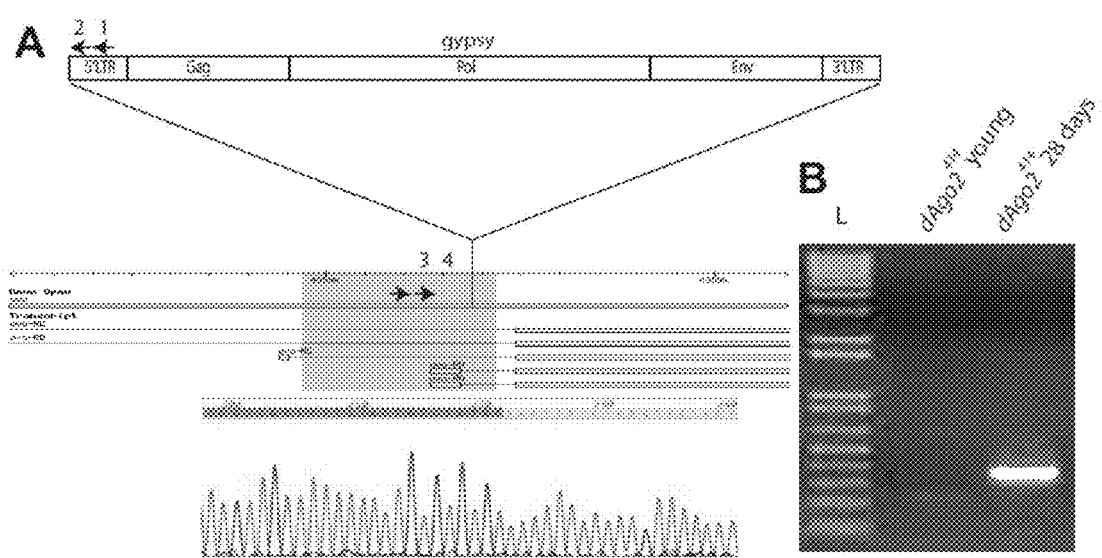
FIG. 6 is an illustration and image of a gel showing s de novo insertion of gypsy into the ovo locus is detected in dAgo2$^{414}$ mutants with genomic PCR. (A) Cartoon of a flybase GBrowse screenshot showing a 2 Kb window of the ovo locus with the location and orientation of the gypsy retrotransposon insertion that was detected by nested genomic PCR. The region of the GBrowse highlighted in gray depicts the sequence present in the "gypsy-TRAP" construct. Sequence results, from clones of the nested PCR fragment from 28-day old dAgo2$^{414}$ fly heads, at bottom show the ovo/gypsy junction with the ovo sequence highlighted in red followed by gypsy sequence in yellow. Arrows represent the primers used for nested PCR. (B) Ethidium bromide stained gel with a 1 Kb plus DNA ladder showing the presence of a 350 bp de novo band from heads of 28-day old dAgo2$^{414}$ mutant animals. This product is not present in young animals. Because the genomic DNA was extracted from whole heads, the possibility cannot be formally excluded of a low rate of de novo insertions in young animals that were not detectable by genomic PCR.
Figure 7:
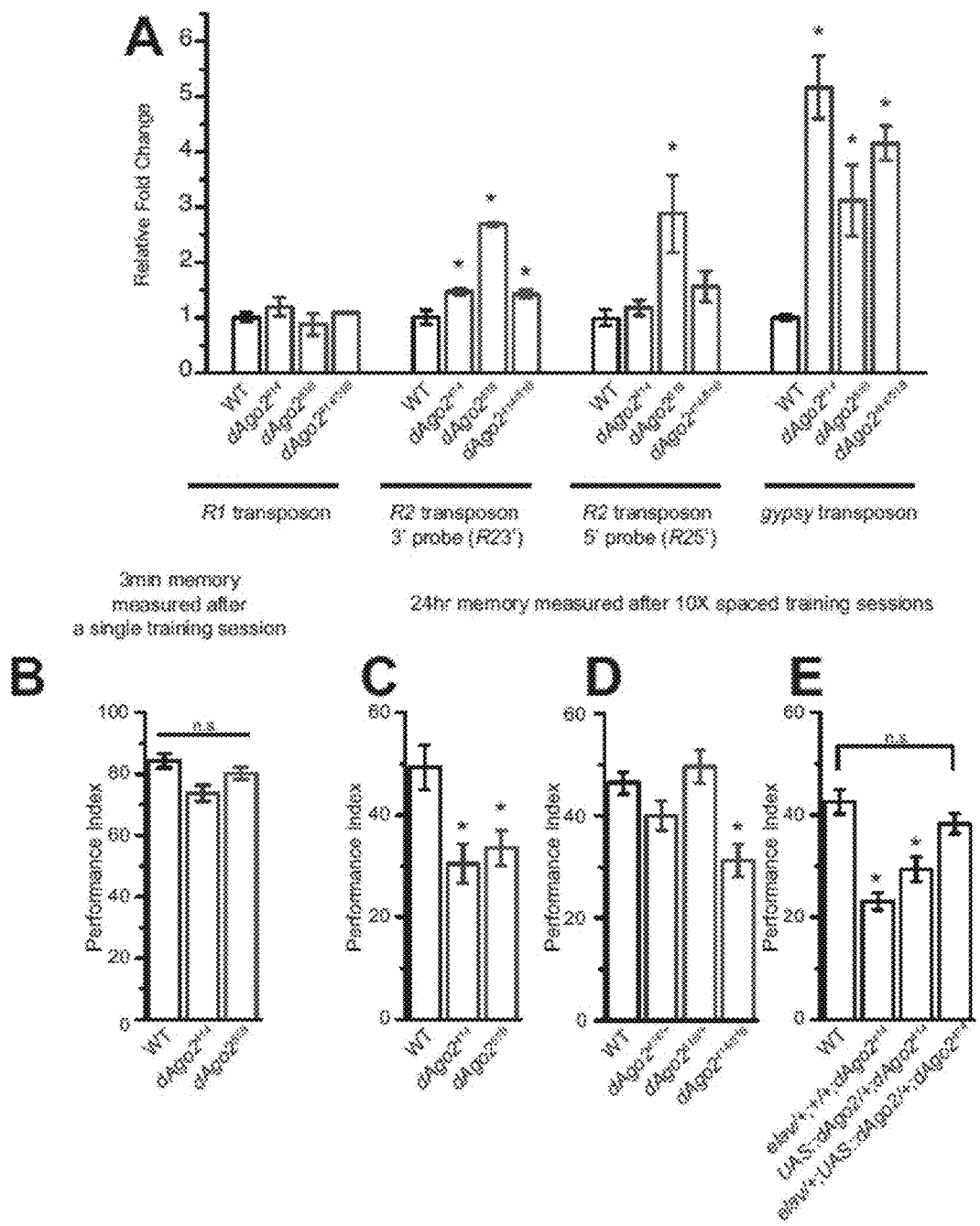
FIG. 7 is a panel of histograms showing that dAgo2 mutants have increased R2 and gypsy expression and defective olfactory memory. (A) Levels of transcripts from R1, R2 and gypsy were quantified indAgo2 mutant animals relative to wild type from 2-4-day old animals. For R2, two independent probes were designed to target the 5' (R25') and 3' (R23') end of the R2 transcript. Significant elevated expression of R23' and gypsy are seen in dAgo2$^{414}$, dAgo2$^{51B}$ and dAgo2$^{414/51B}$ (*, $p<0.05$ and N=4). With R25', a significant increase is seen in dAgo251B (*, $p<0.05$ and N=8). (B-E) Behavioral performance indices (means±SEM) are shown for aversive Pavlovian olfactory memory. (B) dAgo2 mutant animals exhibit normal STM (3 minutes memory measured after one training session) (n.s., not significant and N=8). (C-E) dAgo2 mutant alleles exhibit defective LTM (24 hr memory measured after 10× spaced training (See Methods in the Examples Section herein). (C) Both homozygous dAgo2$^{414}$ and dAgo2$^{51B}$ animals exhibit significantly lower L™ memory performance indices (*, $p<0.05$, N=8) relative to that of WT flies. (D) dAgo2$^{414}$ and dAgo2$^{51B}$ fail to complement each-other for L™ performance as dAgo2$^{414/51B}$ animals exhibit reduced performance (*; $p<0.05$ and N=16) relative to WT controls or to animals that are heterozygous either for dAgo2$^{414}$ or dAgo2$^{51B}$ (E) The LTM defect can be rescued by expressing a UAS::dAgo2 transgene under control of the pan-neuronal e/av-Ga14 line (elav/+; UAS::dAgo2/+; dAgo2$^{414}$). Animals that are homozygous for dAgo2414 and heterozygous for either the e/av-Ga14 line or UAS::dAgo2 (elav/+; +/+; dAgo2$^{414}$ or UAS::dAgo2/+; dAgo2$^{414}$) exhibit defective LTM (*, $p<0.05$ and N=16).
Figure 8A:
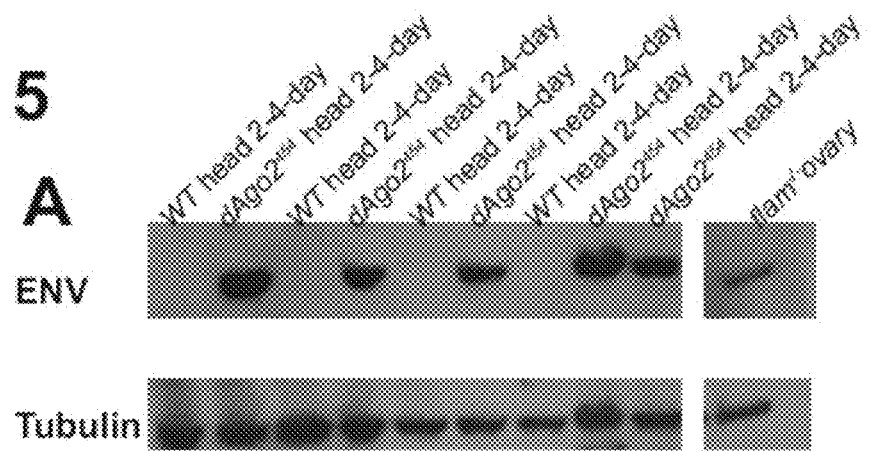
FIG. 8A is a western blot showing the detection of increased gypsy ENV protein level in heads from 2-4-day old dAgo2$^{454}$ animals by western blot. The detected gypsy ENV band from fly heads is identical in size to the gypsy ENV band from flam−/− ovaries.
Figure 8B:
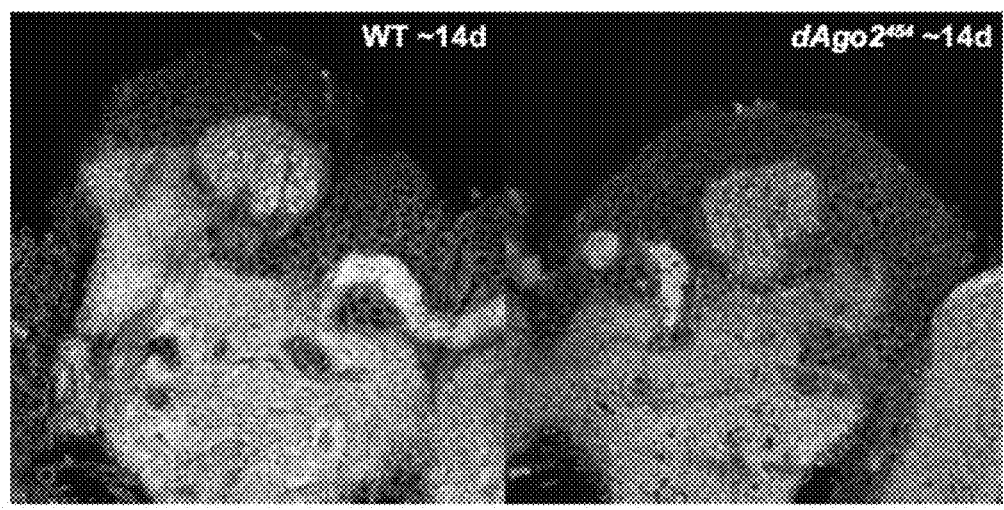
FIG. 8B is an image showing that increased gypsy ENV expression is also detected in whole mount brains from ~14-day old dAgo2$^{454}$ animals by ENV immunolabeling; dAgo2$^{454}$ allele is a recently identified dAgo2 null allele (Hain 2010). Optical sections are shown for ~14-day WT (left panel) and dAgo2$^{454}$ (right panel). Env (RED) and DiD counterstain (grey) are shown. Increased gypsy EN protein expression was also detected in whole mount brains from 0-4 day and ~28 day old dAgo2$^{454}$ animals by ENV immunolabeling (images not shown).

Transcripts from R2 and gypsy were significantly elevated in head tissue of young $dAgo^{2414}$ and $dAgo^{251B}$ mutant animals, as well as in trans-heterozygous $dAgo^{2414/251B}$ animals (FIGS. 7A and 3A). In addition, the age-dependent elevation of both R2 and gypsy expression is accelerated in the dAgo2 mutants such that transcript levels of both R2 and gypsy in 2-4-day old mutant animals are comparable to that seen in ~28-day old wild type animals. At the protein level, the results revealed an accelerated age dependent increase in ENV in dAgo2 mutants (the $dAgo^{2414}$ and $dAgo^{251B}$ hypomorphic alleles and the $dAgo^{2454}$ null allele) both in whole mount brains (FIGS. 3B and 8B) and on western blots from adult heads (FIGS. 3C and 8A). Furthermore, elevated expression of gypsy in dAgo2 mutants also is associated with de novo insertions into the ovo locus, as detected by genomic PCR and sequencing (FIG. 6).

Figure 3D:
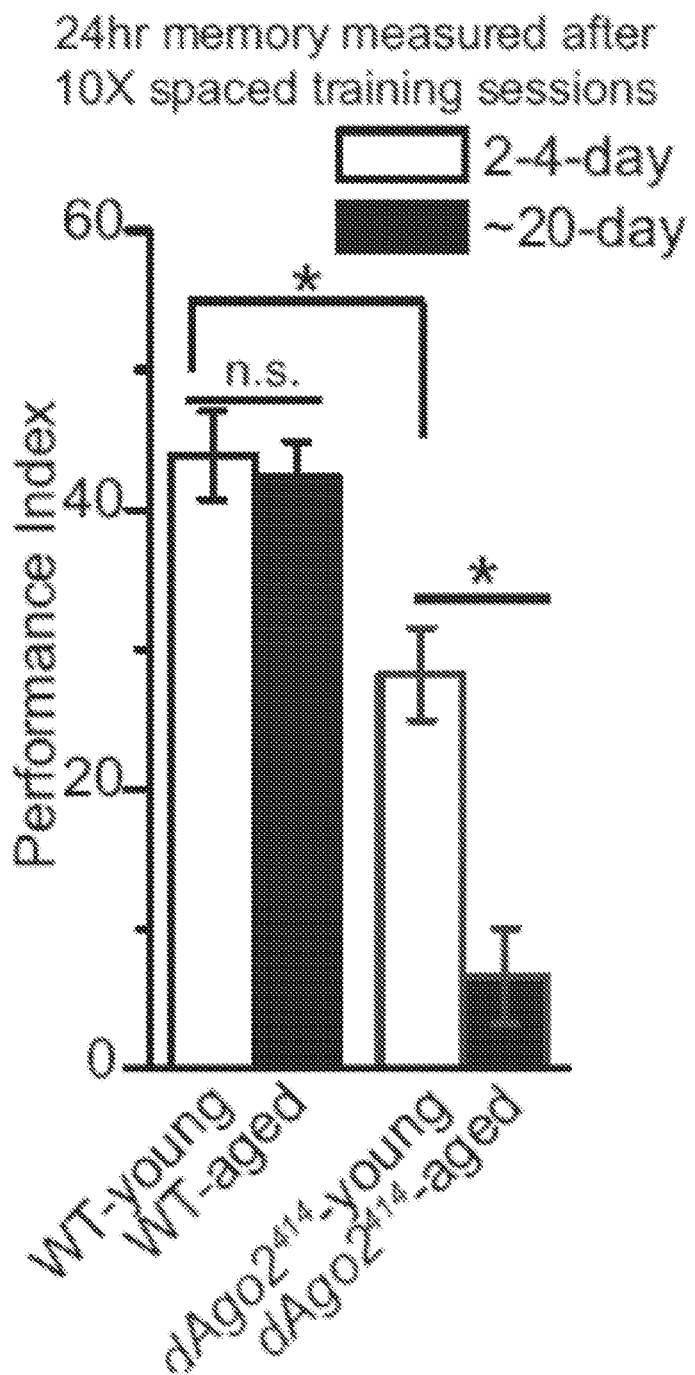
FIG. 3D is a histogram showing LTM performance (means±SEM) for 2-4-day old and ~20-day old WT and dAgo2$^{414}$ mutant animals. 2-4-day old dAgo2$^{414}$ mutants exhibit significantly reduced LTM performance relative to 2-4-day old WT animals, and show a dramatic further reduction in performance in the 20-day old dAgo2$^{414}$ mutant group (*, $p<0.05$ and N=15). The specificity of these results was verified by the analysis of olfactory acuity and shock reactivity, which revealed no differences between the genotypes (data not shown).
Figure 10:
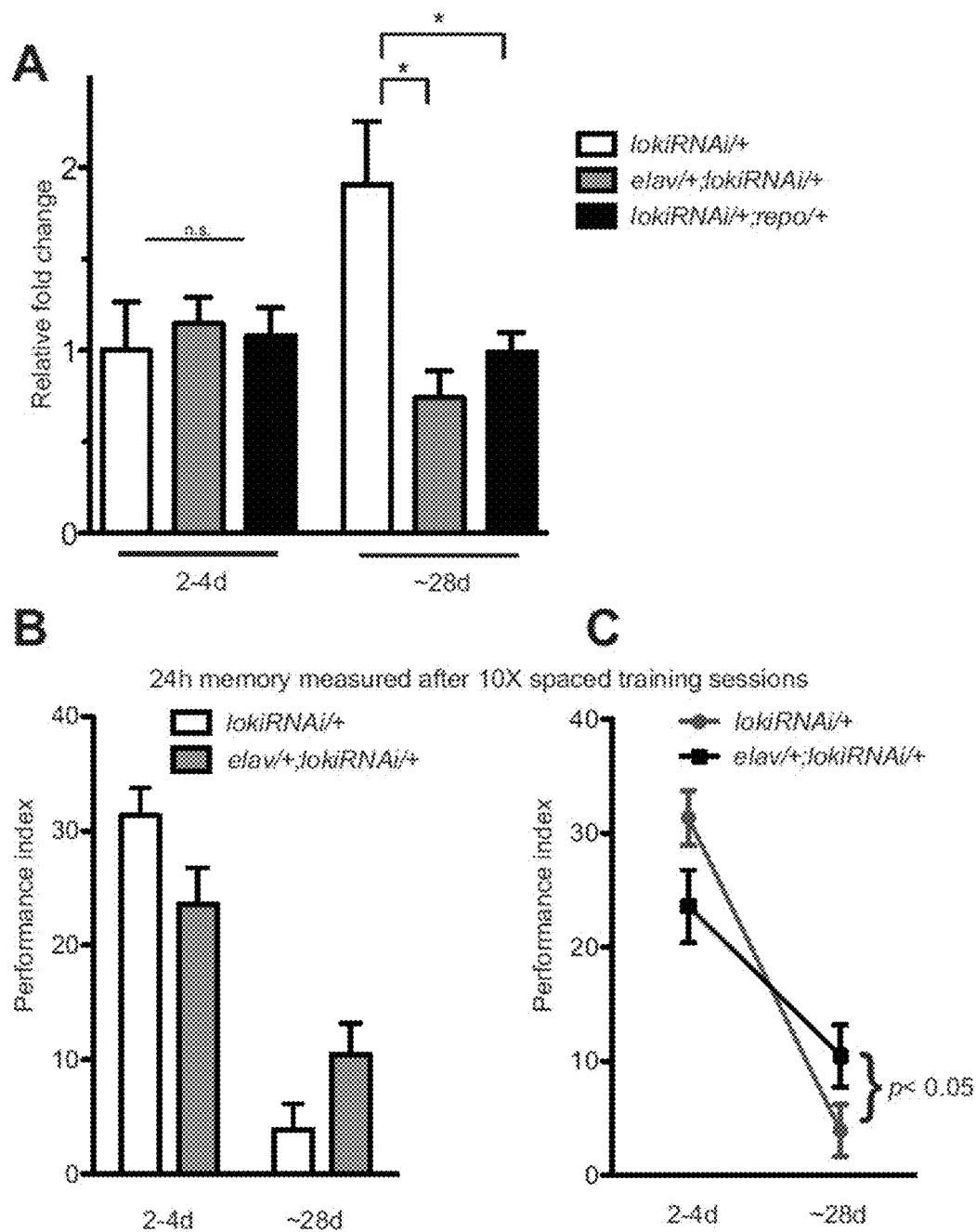
FIG. 10 is a panel of histograms showing that lokiRNAi is effective in suppressing expression of loki, the Drosophila ortholog of Checkpoint kinase 2 (chk2), in heads from ~28-day old animals. When lokiRNAi is expressed in neurons with elav-GAL4 or glia cells with repo-GAL4, reduced loki expression levels are observed in heads from ~28-day old animals (A). However, the effect on lifespan is only observed when lokiRNAi is expressed in neurons with elav-GAL4 (FIG. 3F), but not in glia cells with repo-GAL4 (data not shown). 24 hr memory after 10× spaced training sessions is measured for lokiRNAi/+ and elav/+; lokiRNAi/+ animals at both 2-4-day and ~28-day time point (B,C). The age-dependent memory decline in elav/+; lokiRNAi/+ is significantly smaller than lokiRNAi/+ animals (C and Two-Way ANOVA for age and genotype interaction).

To investigate the correlation between age-dependent neuronal decline and TE activation, a robust and sensitive Pavlovian learning and memory assay was used that is well established in *Drosophila* (Dubnau and Chiang, *Curr. Opin. Neurobiol.* 2013, 23, 84-91. The assay compared 24-hour L™ performance in animals that were trained when they were young (2-4-day) or trained versus when they were at an intermediate age (~20-day). dAgo2 mutants already exhibit a partial reduction in memory at 2-4-days old (FIGS. 7C, 7D, 3D), an effect which can be rescued by neuronal expression of a dAgo2 transgene (FIG. 7E). The mild defect seen in young animals becomes dramatically worse in 20-day old adults (FIG. 3D). In contrast, wild-type animals trained at the ~20-days age exhibited normal robust levels of LTM that are equivalent to that seen in 2-4-day old wild type animals (FIG. 3D), only developing impairment at ~28-day of age (FIG. 10B).

Figure 3E:
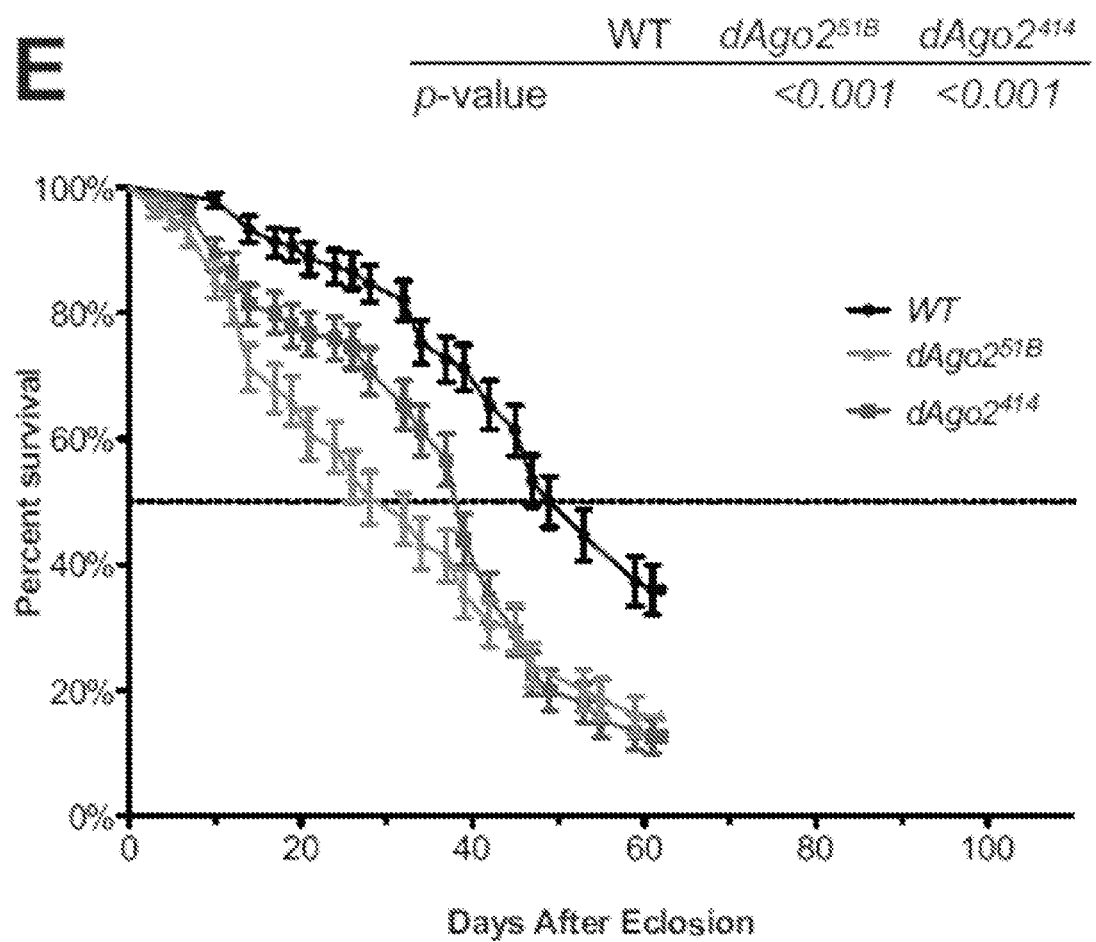
FIG. 3E is a graph showing that lifespan is significantly shortened for dAgo2$^{414}$ and dAgo2$^{51B}$ animals relative to WT (log-rank test).
Figure 8C:
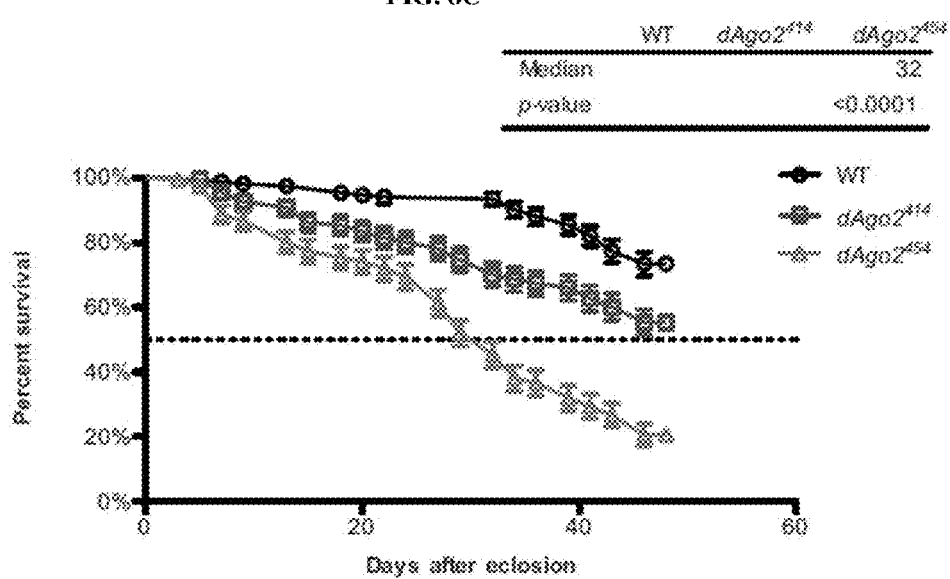
FIG. 8C is a graph showing that compared to wild-type animals, dAgo2$^{414}$ mutants show a shortened lifespan, and dAgo2$^{454}$ mutants show a severely shortened lifespan (log-rank test).
Figure 9A:
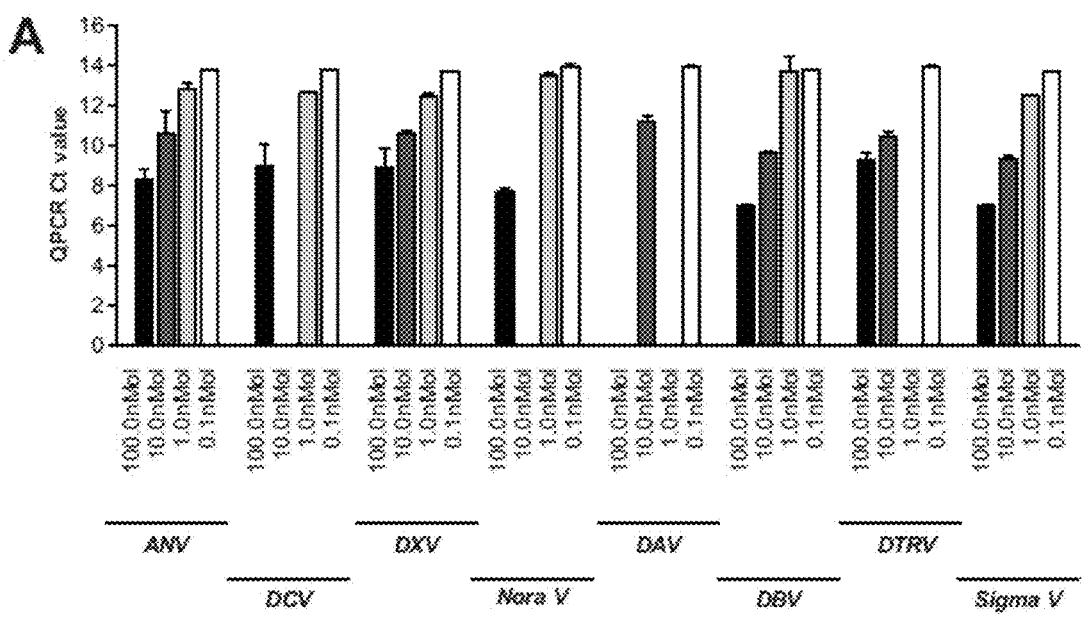
FIG. 9 is a panel of histograms showing examined the expression of the 8 natural viruses that have been detected in Drosophila melanogaster strains and cells (Wu 2010). (A,B) Only one of these, Drosophila C virus (DCV) was detected in our strains, but its expression levels do not correlate with age, genotype or TE expression. (C) By bleach treating embryos, detectable DCV can be eliminated; however, even in the absence of virus following such bleach treatment, age-dependent activation of TEs still occur. (In addition, the effects of dAgo2 on lifespan remain (FIG. 3E)). Thus, the accelerated decline observed in dAgo2 mutants neither correlates with, nor depends upon, presence of exogenous viruses. In contrast, the expression of R2 and gypsy retrotransposons correlates with age dependent decline both in wild type and dAgo2 mutants.
Figure 9B:
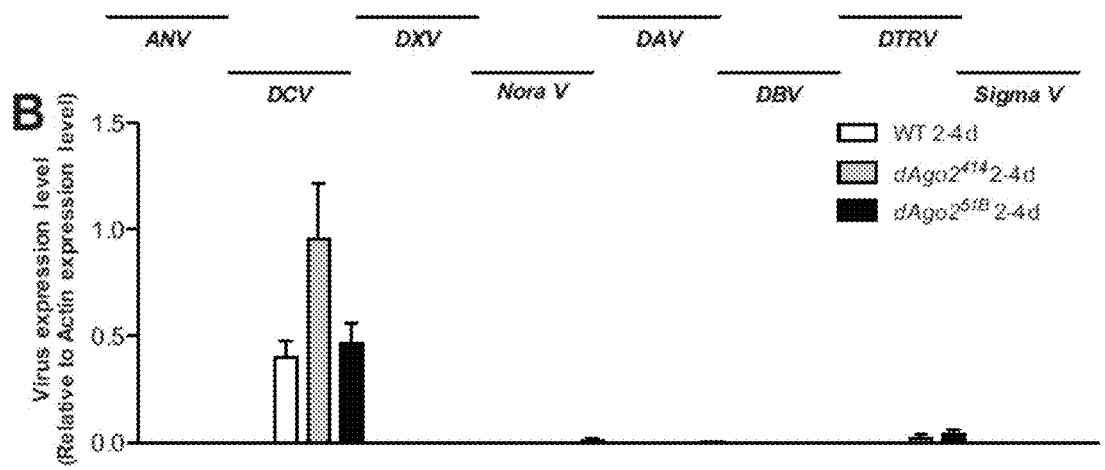
Figure 9C:
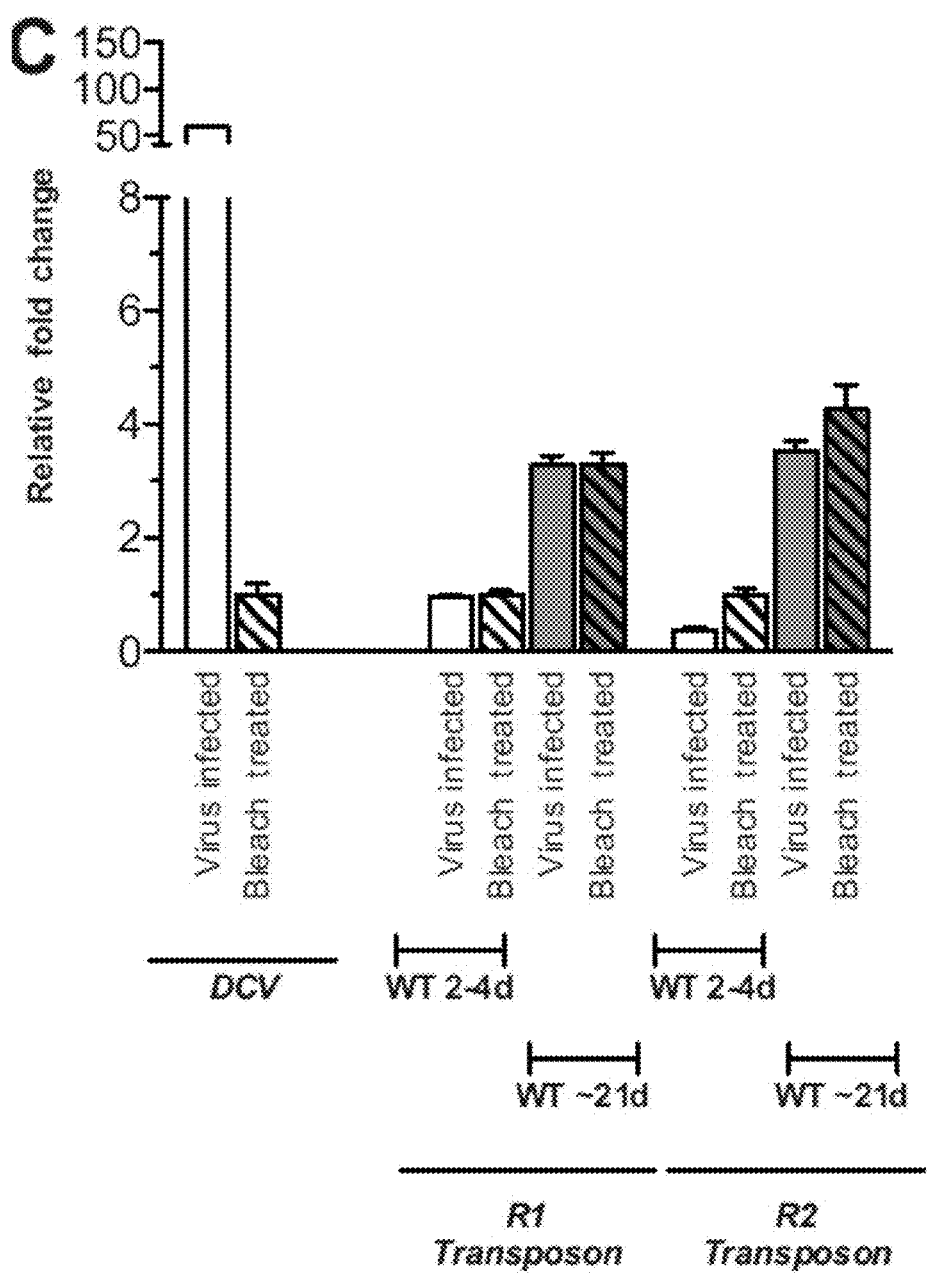

The effects of dAgo2 mutations on longevity were also examined, revealing that dAgo2414, dAgo251B and dAgo2454 mutants exhibited significantly shorter lifespans than their wild type counterparts (FIGS. 3E and 8C). This finding is consistent with reports that mutations in Dicer-218 and loquacious (Liu et al., *Nature*, 2012, 482, 519-523) other components of the somatic small RNA-dependent TE silencing pathway, also exhibit short lifespan. Although dAgo2 mutants are susceptible to exogenous viruses, viral infections do not contribute to the age-dependent decline in these mutants an do not cause the observed induction of transposons (FIG. 9).

Example 3

Inhibiting DNA Damage-Induced-Apoptosis Delays Mortality and age-dependent memory impairments TE activation in the germline is sufficient to cause sterility, at least in part by triggering Checkpoint kinase 2 (Chk2)-mediated DNA damage-induced apoptosis. In fact, disruption of Chk2 in the germline prevents cells from undergoing programmed cell death, which is sufficient to suppress TE dependent sterility (Chen et al., *Curr Biol*, 2007, 17, 637-642).

Figure 3F:
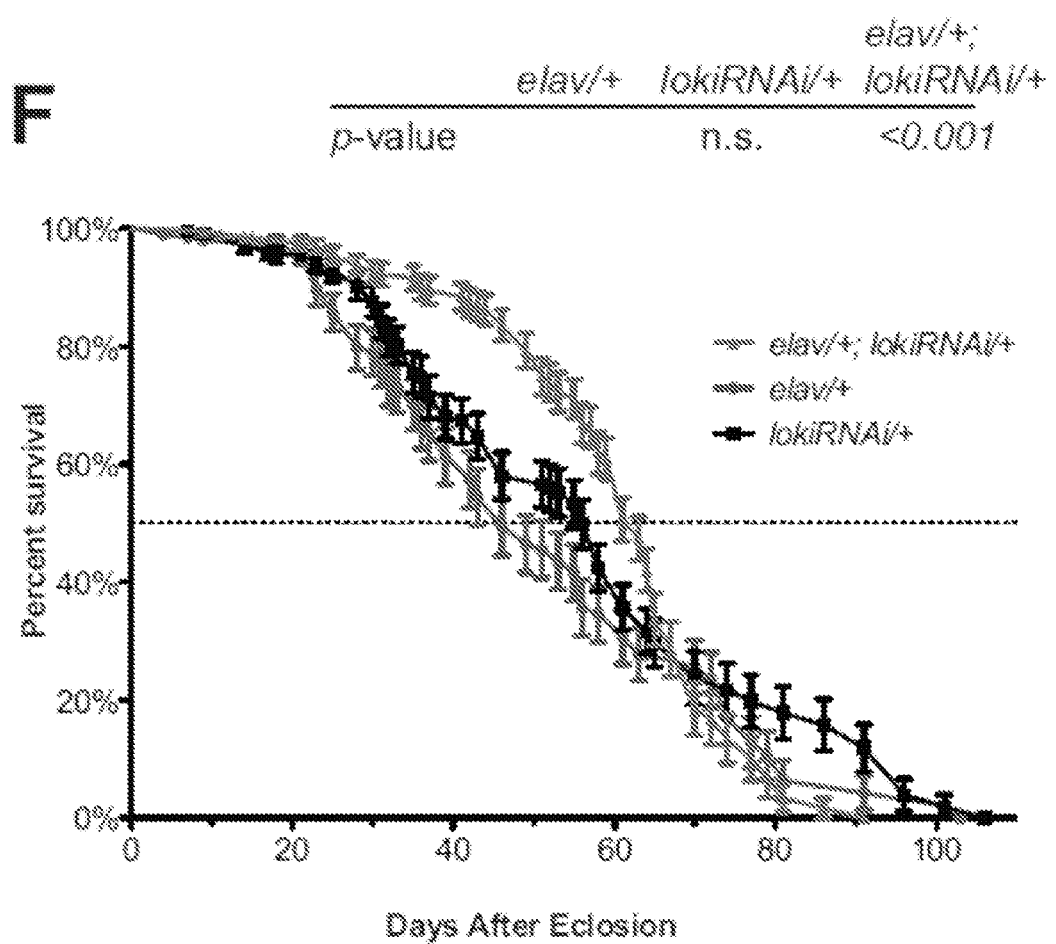
FIG. 3F is a graph showing that knocking down gene expression of loki (the Drosophila ortholog of Checkpoint kinase 2 (chk2)) with loki RNAi in neurons significant delays mortality (Gehan-Breslow-Wilcoxon test) of the elav/+; lokiRNAi/+ animals compared to heterozygous controls for transgenes (elav/+ and lokiRNAi/+). (Such lokiRNAi-mediated knockdown also delays the onset of age-dependent memory decline (FIG. 10)).

To test whether DNA-damage leading to Chk2 signaling also contributes to age dependent mortality in wild type animals, we used an RNAi transgene to target loki, the *Drosophila* ortholog of chk2. Remarkably, disrupting loki function exclusively in neurons by expressing the lokiRNAi under control of the pan-neuronal elav-GAL4 can significantly delay mortality (FIGS. 10A and 3F). Moreover, this disruption of loki function also yields a modest but significant delay in age dependent memory impairment (FIGS. 10B and 10C). These observations are consistent with a causal role for TE activation and TE-induced DNA damage in age-related neuronal decline.

The specification, including the examples, is intended to be exemplary only, and it will be apparent to those skilled in the art that various modifications and variations can be made in the present invention without departing from the scope or spirit of the invention as defined by the appended claims. Furthermore, while certain details in the present disclosure are provided to convey a thorough understanding of the invention as defined by the appended claims, it will be apparent to those skilled in the art that certain embodiments may be practiced without these details. Moreover, in certain instances, well-known methods, procedures, or other specific details have not been described to avoid unnecessarily obscuring aspects of the invention defined by the appended claims.

While certain embodiments are described herein, it will be understood that the described embodiments are not intended to limit the scope of the invention as defined by the appended claims. On the contrary, the present disclosure is intended to cover alternatives, modifications and equivalents that may be included within the spirit and scope of the invention as defined by the appended claims. Furthermore, certain details in the present disclosure are provided to convey a thorough understanding of the invention defined by the appended claims. However, it will be apparent to those skilled in the art that certain embodiments may be practiced without these details. In certain instances, well-known methods, procedures, or other specific details have not been described to avoid unnecessarily obscuring aspects of the invention defined by the appended claims.

---

What is claimed is:

1. A method for determining if a test subject is at higher risk of accelerated age-related neuronal decline and in need of treatment of age-related neuronal decline, the method comprising
   a. measuring expression of at least one retrotransposon in a biological sample from the test subject, and
   b. determining whether the retrotransposon expression measured in step (a) exceeds expression of the retrotransposon in a control subject that is not afflicted with age-related neuronal decline,
   wherein a higher level of retrotransposon expression in the test subject relative to the control subject indicates that the subject is at higher risk of accelerated age-related neuronal decline and is in need of treatment of age-related neuronal decline.

2. The method of claim 1, wherein the subject is in need of treatment with a transposon inhibitor.

3. The method of claim 2, wherein the transposon inhibitor is an inhibitor of a protein encoded by a transposon.

4. The method of claim 3, wherein the protein encoded by the transposon is a transposase; an integrase; a reverse transcriptase; an endonuclease; a protein encoded by gag, pol, or env; an enzyme encoded by ORF1 of a non-LTR transposon; or an enzyme encoded by ORF2 of a non-LTR transposon.

5. The method of claim 2, wherein the transposon inhibitor is an anti-retroviral drug; an inhibitor of reverse transcription; an inhibitor of transposase or integrase activity; an inhibitor of endonuclease activity; a zinc-finger that targets a transposon promoter region; a repressor that inhibits a transposon; an innate antiretroviral resistance factor; a small interfering RNAs (siRNA), short hairpin RNA (shRNA), morpholino, or antisense oligonucleotide directed to a TE transcript; or an inhibitor of post-translational processing or proteolysis of a transposon-encoded protein.

6. The method of claim 1, wherein the retrotransposon includes a gypsy element.

7. The method of claim 1, further comprising administering to the subject an effective amount of a transposon inhibitor.

8. The method of claim 7, wherein the transposon inhibitor is an inhibitor of a protein encoded by a transposon.

9. The method of claim 8, wherein the protein encoded by the transposon is a transposase; an integrase; a reverse transcriptase; an endonuclease; a protein encoded by gag, pol, or env; an enzyme encoded by ORF1 of a non-LTR transposon; or an enzyme encoded by ORF2 of a non-LTR transposon.

10. The method of claim 1, wherein the biological sample in step (a) is contacted with an antibody against a transposon protein.

11. The method of claim 1, wherein the retrotransposon is an LTR retrotransposon.

12. The method of claim 7, wherein the transposon inhibitor is an anti-retroviral drug; an inhibitor of reverse transcription; an inhibitor of transposase or integrase activity; an inhibitor of endonuclease activity; a zinc-finger that targets a transposon promoter region; a repressor that inhibits a transposon; an innate antiretroviral resistance factor; a small interfering RNAs (siRNA), short hairpin RNA (shRNA), morpholino, or antisense oligonucleotide directed to a TE transcript; or an inhibitor of post-translational processing or proteolysis of a transposon-encoded protein.

13. The method of claim 2, wherein the transposon inhibitor is an inhibitor of reverse transcriptase activity.

14. The method of claim 2, wherein the transposon inhibitor is an inhibitor of endonuclease activity.

15. The method of claim 2, wherein the transposon inhibitor is an inhibitor of integrase activity.

16. The method of claim 2, wherein the transposon inhibitor is an anti-retroviral drug.

17. The method of claim 7, wherein the transposon inhibitor is an inhibitor of reverse transcriptase activity.

18. The method of claim 7, wherein the transposon inhibitor is an inhibitor of endonuclease activity.

19. The method of claim 7, wherein the transposon inhibitor is an inhibitor of integrase activity.

20. The method of claim 7, wherein the transposon inhibitor is an anti-retroviral drug.

* * * * *